(12) United States Patent
Geisinger et al.

(10) Patent No.: US 11,523,963 B2
(45) Date of Patent: Dec. 13, 2022

(54) VIRTUAL REALITY APPARATUS AND METHODS THEREFOR

(71) Applicant: LIBRA AT HOME LTD, Jerusalem (IL)

(72) Inventors: Dario Geisinger, Jerusalem (IL); Alberto Saul, Jerusalem (IL); Martin Kohn, Givat Zeev (IL); Shalom Lampert, Maalot (IL)

(73) Assignee: LIBRA AT HOME LTD, Jersalem (IL)

( * ) Notice: Subject to any disclaimer, the term of this patent is extended or adjusted under 35 U.S.C. 154(b) by 379 days.

(21) Appl. No.: 16/476,310

(22) PCT Filed: Jan. 8, 2018

(86) PCT No.: PCT/IB2018/050110
§ 371 (c)(1),
(2) Date: Jul. 8, 2019

(87) PCT Pub. No.: WO2018/127851
PCT Pub. Date: Jul. 12, 2018

(65) Prior Publication Data
US 2019/0365594 A1    Dec. 5, 2019

(30) Foreign Application Priority Data
Jan. 6, 2017  (CA) ...................................... 2953752

(51) Int. Cl.
*A61M 21/00* (2006.01)
*G03H 1/00* (2006.01)
(Continued)

(52) U.S. Cl.
CPC ................ *A61H 5/00* (2013.01); *A61B 3/113* (2013.01); *G06F 3/013* (2013.01); *H04N 5/2254* (2013.01);
(Continued)

(58) Field of Classification Search
CPC .... A61M 21/00; B43L 13/18; G02B 27/0103; G02B 27/145; G02B 27/144;
(Continued)

(56) References Cited

U.S. PATENT DOCUMENTS 8,730,266 B2    5/2014  Brown et al.
9,715,112 B2 *  7/2017  Border ................. G02B 27/017
(Continued)

FOREIGN PATENT DOCUMENTS

CN    106020480 A     10/2016
CN    106020480 A1    10/2016
(Continued)

OTHER PUBLICATIONS

Machine Translation for (by Google Patents) CN106020480 published on Oct. 12, 2016.
(Continued)

*Primary Examiner* — Dawayne Pinkney
(74) *Attorney, Agent, or Firm* — Momentum IP; Marc Van Dyke

(57) ABSTRACT

Virtual reality apparatus, and various methods therefor.

20 Claims, 11 Drawing Sheets

(51) Int. Cl.
 *G02B 27/14*  (2006.01)
 *A61B 3/14*  (2006.01)
 *A61H 5/00*  (2006.01)
 *A61B 3/113*  (2006.01)
 *G06F 3/01*  (2006.01)
 *H04N 5/225*  (2006.01)
 *H04M 1/02*  (2006.01)

(52) U.S. Cl.
 CPC ........... *A61H 2201/0107* (2013.01); *A61H 2201/0188* (2013.01); *A61H 2201/165* (2013.01); *A61H 2201/1607* (2013.01); *A61H 2201/5007* (2013.01); *A61H 2201/5043* (2013.01); *A61H 2201/5097* (2013.01); *H04M 1/0264* (2013.01)

(58) Field of Classification Search
 CPC ........... G02B 27/0172; G02B 27/0149; G02B 27/0025; G02B 27/1013; G02B 27/126; G02C 5/00; G02C 7/02; G02C 7/04; A61B 3/103; A61B 3/14; A61B 3/113; A61B 3/1225; A61B 3/024
 USPC .... 600/27; 359/13, 629–636, 618, 638–640; 351/41, 205, 206, 209, 210, 221, 222, 351/159.01, 159.74–159.76
 See application file for complete search history.

(56) References Cited

U.S. PATENT DOCUMENTS

| | | | |
|---|---|---|---|
| 2002/0096985 A1* | 7/2002 | Hazzard | G03H 1/04 |
| | | | 313/112 |
| 2007/0273968 A1* | 11/2007 | Drodofsky | G02B 23/18 |
| | | | 359/482 |
| 2009/0004029 A1 | 1/2009 | Wegner et al. | |
| 2009/0058660 A1 | 3/2009 | Torch | |
| 2014/0152531 A1 | 6/2014 | Murray et al. | |
| 2014/0232651 A1* | 8/2014 | Kress | G06F 3/013 |
| | | | 345/158 |
| 2015/0326762 A1 | 11/2015 | Ju et al. | |
| 2016/0011424 A1 | 1/2016 | Thurber et al. | |
| 2016/0180591 A1 | 6/2016 | Shiu et al. | |
| 2016/0249805 A1* | 9/2016 | Salvati | A61B 1/0684 |
| | | | 351/206 |
| 2016/0262608 A1 | 9/2016 | Krueger | |
| 2016/0273717 A1* | 9/2016 | Krames | G02F 1/133603 |
| 2016/0349509 A1 | 12/2016 | Lanier et al. | |
| 2017/0092229 A1* | 3/2017 | Greenebaum | G09G 5/10 |
| 2017/0156965 A1 | 6/2017 | Geisinger et al. | |
| 2017/0212352 A1* | 7/2017 | Cobb | G02B 1/041 |
| 2017/0329398 A1* | 11/2017 | Raffle | G02B 27/0093 |
| 2018/0153399 A1 | 6/2018 | Fink | |
| 2020/0374385 A1* | 11/2020 | Kang | H04M 1/185 |
| 2021/0169321 A1 | 6/2021 | Fink et al. | |

FOREIGN PATENT DOCUMENTS

| | | |
|---|---|---|
| CN | 107913165 A | 4/2018 |
| EP | 2814252 A2 | 12/2014 |
| EP | 3257435 A1 | 12/2017 |
| WO | 2016001902 A1 | 1/2016 |
| WO | 2016179370 A1 | 11/2016 |

OTHER PUBLICATIONS

Machine Translation for (by Google Patents) CN107913165 published on Apr. 17, 2018.
International Search Report for PCT/IB2018/050110 dated Jul. 12, 2018.
Written Opinion for PCT/IB2018/050110 dated Jul. 12, 2018.
Extended European (EPO) Search Report for EP3565453 dated Oct. 23, 2020.
Machine Translation (by Google Patents) for CN106020480A published on Oct. 12, 2016.

* cited by examiner

FIG. 6A
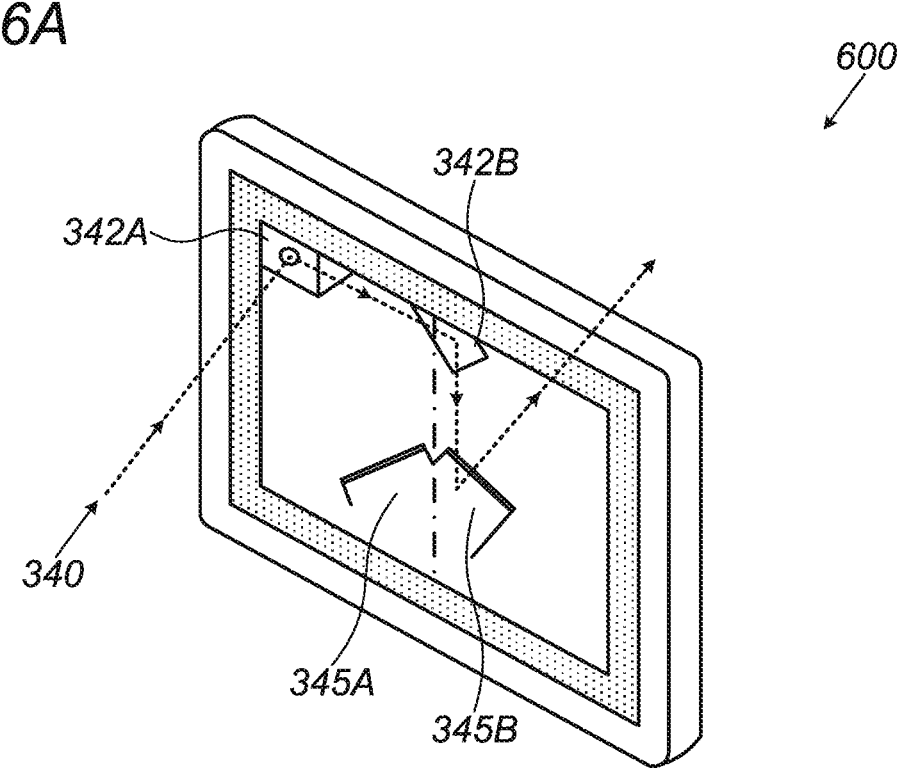
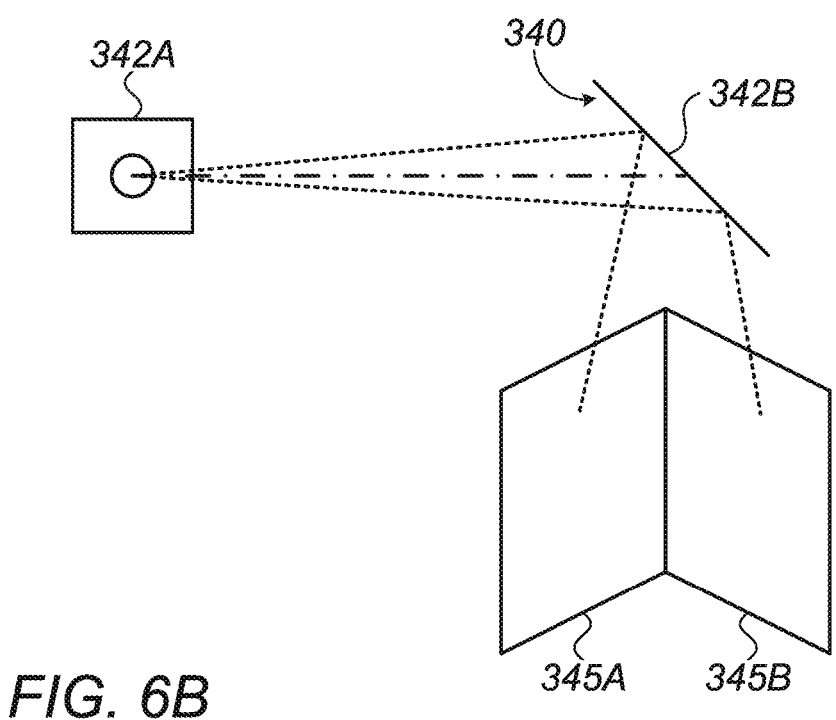
FIG. 6B

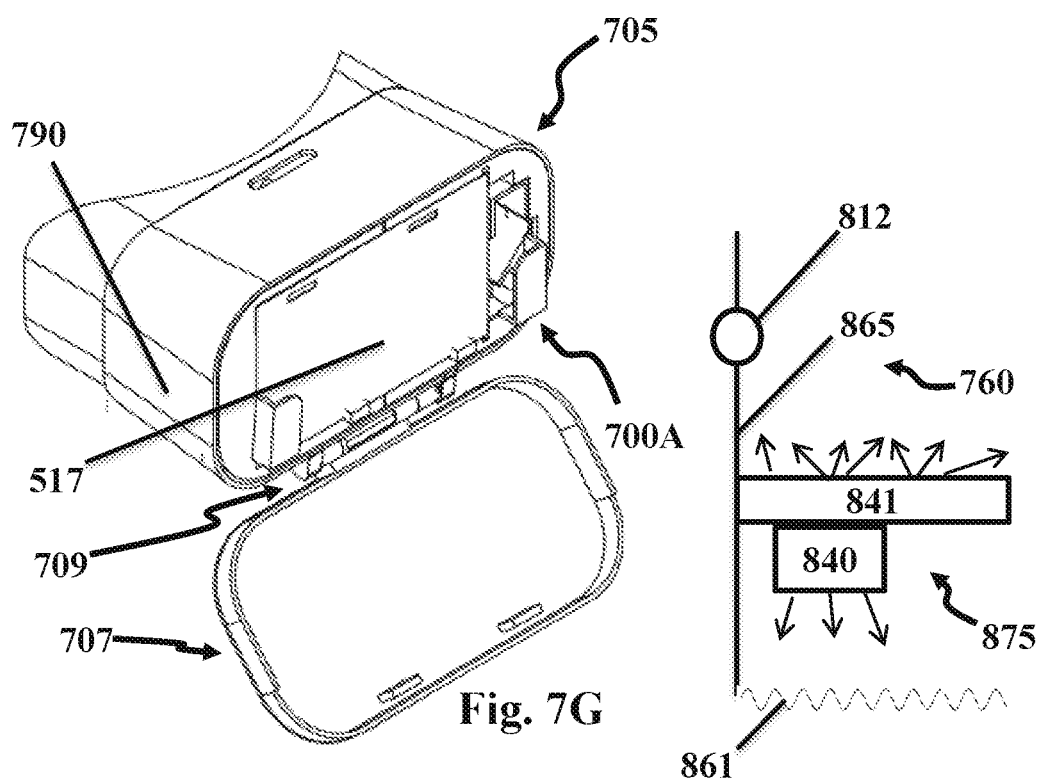
Fig. 7G
Fig. 8A
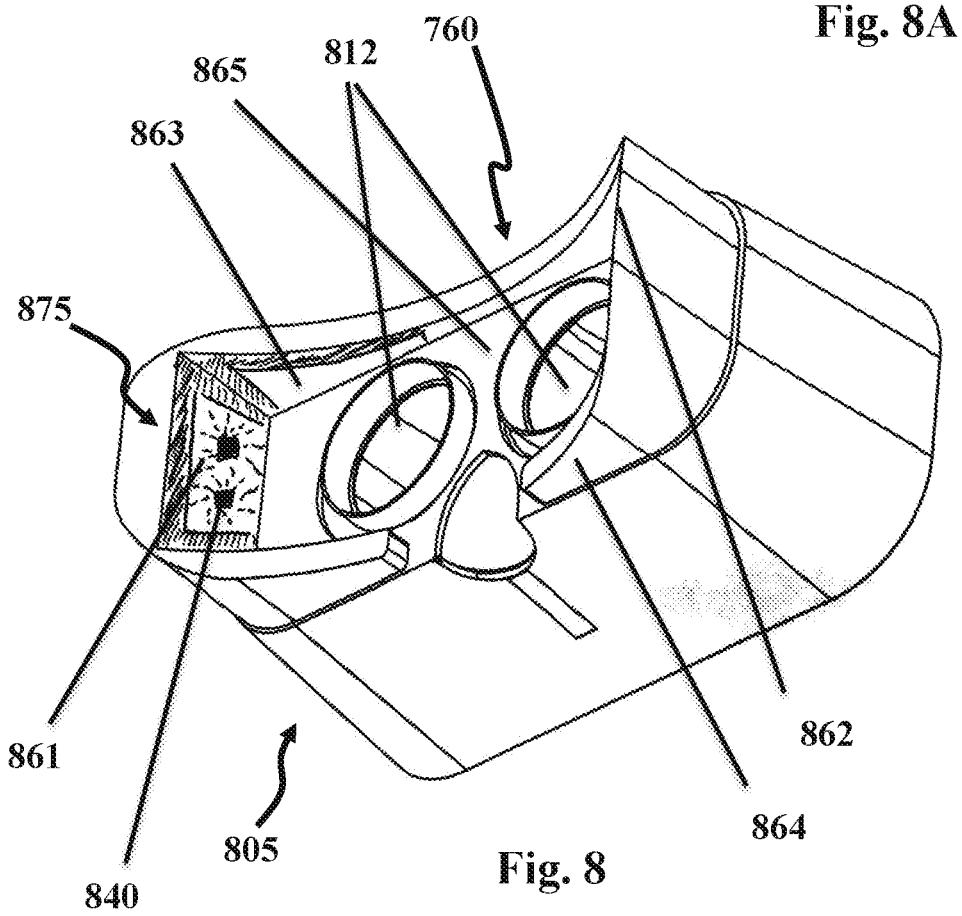
Fig. 8

VIRTUAL REALITY APPARATUS AND METHODS THEREFOR

This application draws priority from Canada Patent Application No. 2,953,752, filed Jan. 6, 2017, which application is incorporated by reference for all purposes as if fully set forth herein.

FIELD AND BACKGROUND OF THE INVENTION

The present invention relates to viewing apparatus such as virtual reality apparatus, and various methods therefor.

Modern electronic devices as well as worldwide connectivity via the Internet have revolutionized many facets of daily life. Communications, commerce, information movement and management have all be dramatically modified with devices such as smartphones and wireless Internet connectivity. One area that will be greatly affected by the convergence of advanced handheld electronic device and Internet connectivity is in the realm of medicine.

Much of modern medicine is practiced in dedicated medical facilities such as hospitals and clinics. The requirement for both medical experts such as doctors and nurses as well as equipment that can often run into the millions of dollars generally leaves medical treatment at dedicated medical facilities. The challenges of the current arrangement are many: the requirement for travel to a hospital or the like; the general requirement to wait a long time for an appointment as there are too many patients relative to the number of medical professionals; an inability to continue a treatment seriously at home due to the lack of the expensive, sophisticated equipment; and, expense—hospital and similar treatments cost a great deal, whether the patient and/or his/her insurance picks of the tab for various treatments. Bills reaching tens of thousands of dollars for simple surgeries are not uncommon.

While all medical treatments are not necessarily amenable to off-site performance, the proper use of advanced electronic devices such as tablets and smartphones, combined with Internet communication with medical professionals offers the possibility of patients performing many activities away from a formal hospital or clinical setting. Off-the-shelf devices combined with dedicated software and, where required, hardware will allow for many patients to perform exercises at home or at say a nursing home, while a nurse or doctor enjoys real-time access to performance data. The possibility of a medical professional modifying a protocol from afar means that many of the bottlenecks present at hospitals and clinics could be removed.

U.S. patent application Ser. No. 13/477,317 to Luberski and Sumango teaches a system and method for use in moderating symptoms associated with vestibular disorders. The patient stands atop a balance platform and balances or performs other exercises on the platform. The exercises require the patient to work against the instability of an inflatable bladder positioned beneath the balance platform. Training difficult may be increased or decreased by changing the pressure of the inflatable bladder. Increased pressure makes the bladder firm, which is easier to balance upon and decreased pressure softens the bladder, making it more difficult to balance upon. Over time, the repeated performance of the exercise sessions improves the impairment the patient is experiencing due to the symptoms of the vestibular disorder.

U.S. patent application Ser. No. 09/909,084 to Stewart and Wallace describes standardized guidelines for diagnosis and treatment of central nervous system abnormalities such as concussions, head trauma, memory loss, confusion, or other cognitive dysfunction. An initial assessment is made of the person for loss of consciousness, spinal cord injury, or a secondary injury. The person is asked to perform a plurality of mental and physical exercises. A dynamic visual acuity test is also taken. These tests can be performed on the sideline of an athletic playing field to determine whether or not. It is advisable for an athlete to return to play. Next, machine-based hearing, dynamic-vision, and balance tests are administered to the patient. The results of these machine-based tests are transmitted electronically to an online database and evaluated by a physician at an off-site location, who prescribes a treatment regimen designed to improve the patient's vestibular functioning.

International Patent Application No. PCT/US2009/040486 to Santina, et al. describes systems and methods for testing vestibular and oculomotor function. One aspect of the invention provides a vestibular and oculomotor function testing device including a track supported by a plurality of hearings, an engine configured to selectively displace the track, and a head coupling component coupled to the track. The head coupling component is configured to convey a movement generated by the engine to a subject's head in one or more axes.

Methods and apparatuses for rehabilitation, particularly for balance and vestibular disorders include BNAVE (Medical Virtual Reality Center University of Pittsburgh) and Balance Quest (Micromedical Technologies), although these systems are unable to perform real-time fusion of visual and vestibular interaction and updating of the displayed image. Equitest (Neurocom, a division of Natus) provides only limited training capabilities. MedFit (Korebalance) provides diagnostic and rehabilitation opportunities and the BRU (Medicaa, Uruguay) provides rehabilitation capabilities, although it is not fit for home use, it is not a portable device and does not incorporate real 3D stimulation nor specific adaptive eye training. Current classic methods for vestibular rehabilitation do not incorporate any technology. In all mentioned cases, there is no way to track home activities and customize the rehabilitation upon home use results.

Balance analysis tools include devices that measure the posture subjected to different sorts of visual, vestibular and proprioceptive stimulation and gait analysis tools by means of accelerometers or cameras that measure different gait parameters while walking on the floor, mattress or treadmill. Examples of posture analysis include Balance Quest (Micromedical Technologies), Balance Manager (Neurocom, a division of Natus) with the Sensory Organization Test (SOT), MedFit (Korebalance), BRU (Medicaa, Uruguay). Gait analysis examples include SensoGo (SensoGo, Israel) and Opal (APDM) that use accelerometer data, while other techniques include cameras recording the body movements, pressure sensing mattresses and gaming hardware such as Kinect (Microsoft). Pressure systems include Walkway (Tekscan) that senses feet pressure.

There is an increase in wellness devices as well that track body movements such as Moov (Mushroom Labs) and Up (Jawbone) which are generally realized as wrist bands.

US Patent Publication Nos. 2006/0206175 and 2009/0240172 disclose methods and apparatus for enabling selective stimulation of oculomotor reflexes involved in retinal image stability.

These advances notwithstanding, the present inventors have recognized a need for improved methods and apparatus for virtual reality viewing, and in particular, for virtual reality viewing methods and apparatus for treating brain-related impairments such as vestibular impairments.

SUMMARY OF THE INVENTION

According to teachings of the present invention there is provided a viewing apparatus comprising a headset adapted to be fixed, in a headset donning mode, on, or with respect to, a head of a user; the headset including at least one viewing lens for at least one of the eyes of the user, so as to view a display screen of a mobile computing device, a holding case adapted to fixedly hold the mobile computing device and to reversibly attach to the headset; an optical arrangement associated with the holding case and with the headset, and including at least one optical angle modifier and at least one optical splitter; the headset, the holding case, and the optical arrangement adapted such that, in a viewing configuration of the donning mode, in which the mobile computing device is inserted in the holding case, a display screen of the mobile computing device faces the at least one viewing lens of the headset; wherein the optical arrangement is further adapted to simultaneously establish, in the viewing configuration, a first optical path between the at least one viewing lens of the headset and the camera lens of the mobile computing device; and a second optical path between the display screen of the mobile computing device and the at least one viewing lens of the headset; wherein the at least one optical splitter is optically disposed on the first optical path, between the viewing lens and the at least one optical angle modifier; wherein the at least one optical angle modifier is optically disposed on the first optical path, between the at least one optical splitter and the camera lens; and wherein the at least one optical angle modifier is adapted to modify an angle of incident light received via the at least one optical splitter, and to direct the light towards the camera lens.

According to teachings of the present invention there is provided a monolithic optical adapting arrangement, substantially as described herein.

According to teachings of the present invention there is provided an apparatus for treatment of vestibular, ocular or central impairment, the apparatus comprising: a headset adapted to sit in a donning mode, on a head of a user; a mobile computing device having a computer processor, at least one camera, and a display screen; a case adapted to hold the mobile computing device and to attach to the headset; an optical arrangement associated with the case or the frame, and adapted to focus a field of view of the at least one camera; and an application associated with the processor, the application and the processor adapted to display at least one stimulation exercise on the screen, using virtual reality; the headset, the case, and the optical arrangement adapted such that, in the donning mode: the screen faces eyes of the user, and the optical arrangement focuses a field of view of the at least one camera onto at least one of the eyes; wherein, with the head in the donning mode, the application is further adapted to record movements of at least one of the eyes, using the at least one camera, during the at least one exercise; and wherein the application is further adapted to: perform a determination of a response competence of the user to a particular stimulation exercise of the at least one stimulation exercise, at least partially based upon the movements; and modify a degree of difficulty of the particular stimulation exercise, based upon the determination.

According to another aspect of the present invention there is provided a method for treating a vestibular, ocular, or central impairment of a patient, the method comprising the steps of placing the headset on the head of the user, the case holding the mobile computing device and attached to the headset; focusing the field of view of the at least one camera onto at least one of the eyes, using the optical arrangement; displaying the at least one stimulation exercise on the screen, by means of the virtual reality; recording or measuring the movements of at least one of the eyes, using the at least one camera; performing the determination of the response competence to the particular exercise, at least partially based upon the movements; and modifying the degree of difficulty of the particular exercise, based upon the determination, to produce a difficulty-modified exercise.

According to yet another aspect of the present invention there is provided a method for generating a vestibular or eye rehabilitation protocol comprising: providing at least one stimulus to eyes of a patient; effecting at least one variation of one or more stimulus parameters of the stimulus; tracking at least one of eye, head and body movement of the patient, during the variation, to quantitatively determine a competence of the patient; and creating a stimulation protocol where a determined stimulus parameter is adapted to begin from a value below the competence and to subsequently increase in difficulty.

According to yet another aspect of the present invention there is provided a method for treating a vestibular, ocular, or central impairment of a patient, the method comprising: placing a headset on a head of the patient, the headset including a mobile computing device adapted to include a touch screen, an accelerometer, at least one camera, a computer processor and a digital memory associated therewith, a wireless communication component and an application adapted to run on the mobile computational device, such that the touch screen is disposed in proximity to eyes of the patient, and such that an optical element associated with the headset directs a focus of the at least one camera towards the eyes; providing the patient with a plurality of eye stimuli and head exercises via the touch screen, according to a first protocol, in a particular therapeutic session; recording responses of the eyes and the head to the stimuli using the at least one camera; storing the responses in the memory and analyzing the responses using the computer processor; continuously monitoring the patient performance in response to stimuli by means of head, eye, and body tracking; producing a correlation of expected performance as predicted by the application with an actual performance measured by the processor; and, at least partially based on the correlation, generating a revised protocol for the patient for additional exercises to improve the actual performance.

According to yet another aspect of the present invention there is provided a viewing apparatus comprising: (a) a headset having at least one viewing lens and adapted to be juxtaposed, in a viewing mode, to a face of a user, such that an eye of the user is aligned with the viewing lens; (b) an adaptor arrangement adapted to fixedly hold a cellphone equipped with at least one camera lens, and to reversibly attach to the headset, the adaptor arrangement including: (i) a cellphone receiving arrangement for fixedly receiving the cellphone in a viewing position; and (ii) an on-board optical arrangement including at least one optical angle modifier; and (c) an optical splitter, disposed within the viewing apparatus; the headset, the cellphone receiving arrangement, and the optical arrangement adapted such that, in a viewing mode, in which the adaptor arrangement is reversibly attached to the headset, and in which the cellphone is fixed in the viewing position, a display screen of the cellphone faces the at least one viewing lens of the headset; wherein the optical splitter and the on-board optical arrangement are adapted to simultaneously establish, in the viewing mode, a first optical path between a first viewing lens of the at least one viewing lens of the headset and at least first camera lens of the at least one camera lens; and a second optical path between the display screen of the cellphone and the first viewing lens; wherein the optical splitter is optically disposed on the first optical path, between the viewing lens and the at least one optical angle modifier; wherein the at least one optical angle modifier is optically disposed on the first optical path, between the at least one optical splitter and the first camera lens; and wherein the at least one optical angle modifier is adapted to modify an angle of incident light received via the at least one optical splitter, and to direct the light towards the first camera lens.

According to still further features in the described preferred embodiments, the apparatus further comprises the mobile computing device, the mobile computing device further including a computer processor adapted, during a viewing event in the viewing mode, to record eye movement information of at least one of the eyes, using the camera lens of the mobile computing device.

According to still further features in the described preferred embodiments, the processor is adapted, during a viewing event in the viewing mode, to display at least one stimulation exercise on the screen, using virtual reality, and to record eye movement information of at least one of the eyes, using the camera lens of the mobile computing device.

According to still further features in the described preferred embodiments, the processor is further adapted to: perform a determination of a response competence of the user to a particular stimulation exercise of the at least one stimulation exercise, at least partially based upon the movements; and modify a degree of difficulty of the particular stimulation exercise, based upon the determination.

According to still further features in the described preferred embodiments, the determination of the response competence is further based upon at least one of a normative response competence and a previous response competence of the user.

According to still further features in the described preferred embodiments, the at least one optical splitter includes a beamsplitter.

According to still further features in the described preferred embodiments, the at least one optical angle modifier includes at least one mirror.

According to still further features in the described preferred embodiments, the headset includes a viewing recess.

According to still further features in the described preferred embodiments, the viewing recess is adapted such that, with a face of the user juxtaposed thereto in the viewing mode, a viewing chamber is formed.

According to still further features in the described preferred embodiments, the apparatus further comprises a light source arrangement including a light source, and adapted, in the viewing mode, to provide light within the viewing recess.

According to still further features in the described preferred embodiments, the light source is directed towards an inner wall of the viewing recess.

According to still further features in the described preferred embodiments, the light source arrangement includes a light diffuser, optically disposed between the light source and at least one of the viewing lens and a position of the eye of the user, when viewing through the viewing lens, in the viewing mode.

According to still further features in the described preferred embodiments, the light source includes a light-emitting diode (LED).

According to still further features in the described preferred embodiments, the light source includes a flash from the cellphone, and the light source arrangement includes an optical conduit for delivering light from the flash to the viewing recess.

According to still further features in the described preferred embodiments, the optical splitter is a glass plane having partial reflectivity, optionally within a range of 2 to 30%.

According to still further features in the described preferred embodiments, at least in the viewing mode, the optical arrangement is disposed in an optical chamber.

According to still further features in the described preferred embodiments, at least one internal wall of the optical chamber is a light-absorbing wall that is black and/or matte.

According to still further features in the described preferred embodiments, the optical arrangement is a first optical arrangement, the apparatus further comprising a second optical arrangement according to any one of claims 1 to 17, the second optical arrangement being optically separate or parallel to the first optical arrangement, and forming an optical path with a second viewing lens of the at least one viewing lens of the headset.

According to still further features in the described preferred embodiments, the second optical arrangement is adapted to form an optical path with the identical camera lens of the cellphone.

According to still further features in the described preferred embodiments, the second optical arrangement is adapted to form an optical path with a second camera lens of the cellphone.

According to still further features in the described preferred embodiments, the first and second optical arrangements are optically separated by a partition wall.

According to still further features in the described preferred embodiments, the apparatus further comprises a cellphone screen filter optically disposed between the cellphone screen and the optical splitter, and adapted and oriented to filter at least a portion of low-angle light emanating from the screen in the direction of the optical angle modifier closest to the camera lens, the low-angle light being at most 50°.

According to still further features in the described preferred embodiments, the optical splitter is part of the adaptor arrangement.

According to still further features in the described preferred embodiments, the adaptor arrangement is a monolithic adaptor arrangement.

According to still further features in the described preferred embodiments, the adaptor arrangement includes at least one fastening element adapted to secure the adaptor arrangement to the headset.

According to still further features in the described preferred embodiments, the adaptor arrangement is adapted to fix a particular cellphone in a single or pre-determined position.

According to still further features in the described preferred embodiments, the camera lens of a particular cellphone is disposed in a particular position, and wherein the adaptor arrangement, including the onboard optical arrangement, is adapted for the particular cellphone and the particular position of the camera lens, such that, with the particular cellphone fixed in the viewing position, the optical angle modifier nearest the camera lens is optically aligned with the camera lens, both being disposed on the first optical path.

According to still further features in the described preferred embodiments, the determination of the response competence is further based upon a target response competence.

According to still further features in the described preferred embodiments, the application is further adapted to perform a determination of a threshold response competence of the user to the particular stimulation exercise.

According to still further features in the described preferred embodiments, the apparatus further comprises at least one accelerometer, at least one of the accelerometer optionally disposed within the mobile computing device.

According to still further features in the described preferred embodiments, the application is further adapted to measure movements of the head, using the at least accelerometer, during at least one head exercise; and the application is further adapted to perform a head-movement based determination of a response competence of the user to a specific head exercise of the at least one head exercise, at least partially based upon the movements of the head; and to modify a degree of difficulty of the specific head exercise, based upon the head-movement based determination.

According to still further features in the described preferred embodiments, the apparatus further comprises at least one of a speaker and a microphone, and the application is further adapted to at least one of: receive user feedback via the microphone and communicate with the user via the speaker during any of the exercises.

According to still further features in the described preferred embodiments, the mobile computing device is a component of the viewing apparatus, the mobile computing device further including a computer processor.

According to still further features in the described preferred embodiments, the processor is adapted, during a viewing event in the viewing configuration, to record eye movement information of at least one of the eyes, using the camera lens of the mobile computing device.

According to still further features in the described preferred embodiments, the processor is adapted, during a viewing event in the viewing configuration, to display at least one stimulation exercise on the screen, using virtual reality.

According to still further features in the described preferred embodiments, the processor is adapted, during a viewing event in the viewing configuration, to record eye movement information of at least one of the eyes, using the camera lens of the mobile computing device.

According to still further features in the described preferred embodiments, the processor is further adapted to perform a determination of a response competence of the user to a particular stimulation exercise of the at least one stimulation exercise, at least partially based upon the movements; and modify a degree of difficulty of the particular stimulation exercise, based upon the determination.

According to still further features in the described preferred embodiments, the determination of the response competence is further based upon a normative response competence.

According to still further features in the described preferred embodiments, the determination of the response competence is further based upon a previous response competence of the user.

According to still further features in the described preferred embodiments, at least a portion of the optical arrangement is built into a monolithic optical adapting arrangement.

According to still further features in the described preferred embodiments, the monolithic optical adapting arrangement includes at least one fastening element adapted to secure the monolithic optical adapting arrangement to the headset.

According to still further features in the described preferred embodiments, the headset includes at least one light source.

According to still further features in the described preferred embodiments, the at least one optical splitter includes a beam splitter and/or a hot mirror.

According to still further features in the described preferred embodiments, the at least one optical angle modifier includes at least one mirror.

According to still further features in the described preferred embodiments, the mobile computing device is selected from the group consisting of a smartphone, tablet computer, digital music player, digital personal assistant, laptop, and mobile computer.

According to still further features in the described preferred embodiments, the mobile computing device is a smartphone.

According to still further features in the described preferred embodiments, the apparatus further comprises a second computing device adapted to receive data from the mobile computing device.

According to still further features in the described preferred embodiments, the mobile computing device is adapted to transfer data and instructions with a remote computing device.

According to still further features in the described preferred embodiments, the apparatus further comprises a database of performance behavior, associated with the computer processor.

According to still further features in the described preferred embodiments, the database includes data pertaining to at least one of: normative performance behavior; performance behavior of users within the same category or having the same profile, and previous performance behavior for the user.

According to still further features in the described preferred embodiments, the is utilized by the processor for at least one of creation, adjustment, customization, and personalization of the at least one stimulation exercise or the at least one head exercise.

According to still further features in the described preferred embodiments, the optical element includes at least one mirror and at least one illumination element arranged to focus the field of view.

According to still further features in the described preferred embodiments, the mobile computing device is adapted to recognize the user according to an eye appearance of the user.

According to still further features in the described preferred embodiments, the headset and the case form a single, integral, monolithic unit.

According to still further features in the described preferred embodiments, the method further comprises applying the difficulty-modified exercise to the user.

According to still further features in the described preferred embodiments, all of the method steps are performed within a single therapeutic session.

According to still further features in the described preferred embodiments, the step of applying the difficulty-modified exercise to the user is performed in a subsequent therapeutic session.

According to still further features in the described preferred embodiments, the method is performed in a home setting.

According to still further features in the described preferred embodiments, the method is performed devoid of clinicians.

According to still further features in the described preferred embodiments, the method is performed devoid of clinical supervision.

According to still further features in the described preferred embodiments, the method is applied to Parkinson's Disease, Multiple Sclerosis, risk of fall, migraine related vertigo, concussions or TBI, anxiety disorders, dizziness, phobic postural vertigo and motion sickness.

According to still further features in the described preferred embodiments, the method is applied to a sensory integration deficit involving eyes, head, neck and/or vestibular information.

According to still further features in the described preferred embodiments, the method is applied to children with peripheral disorders, learning disabilities and/or ADHD.

According to still further features in the described preferred embodiments, the method is applied for peripheral vision, vision improvement in health and pathological subjects, reading speed, vision in age-related macular degeneration and/or cognitive control in depression patients.

According to still further features in the described preferred embodiments, the method further includes adding augmented reality data to the screen via a or the second camera associated with the mobile computing device.

Unless otherwise defined here or in the embodiments, all technical and/or scientific terms used herein may have their same meaning as commonly understood by one of ordinary skill in the art to which the term pertains.

"Vestibular", "ocular", and "central" as they relate to brain-related impairments may have their generally understood meaning in the art. "Goggles" may generally refer to an element adapted to be placed on a patient's head and allow for placement of a portion of goggles or associated elements in front of the patient's eyes. A "case" or "goggle case" may generally refer to an element adapted to be attached to a mobile computing device and further allow for attachment of the goggle case to the goggles. A "mobile computing device" may generally refer to a device or element adapted to perform computational actions. Non-limiting examples of a mobile computing device include smartphones, hand-held computers, Google Glass, smart watches, tablet computers, laptop computers, and the like.

An "optical element" or "optical arrangement" may generally refer to an element adapted to allow focus of a patient's eye(s) towards a camera associated with a mobile computing device, like a smartphone. An optical element may generally include mirrors, lights, or other features that allow for monitoring of patient's eye(s) while patient is involved in exercises associated with a protocol according to the instant invention.

"Protocol" may generally refer to a program, application, procedure, or set of instructions adapted to be presented to a patient for performance in the form of exercises. A protocol may be presented automatically or under control of patient or a medical professional. A protocol may be adapted, modified, changed, or altered based on performance of exercises associated with the protocol.

A "headset" may generally refer to a headgear element or arrangement. The headset may be adapted to enable the presentation of eye exercises to the eyes of the user, during a donning mode. The headset may allow for tracking of the eyes. Additionally, the headset may allow for tracking of other features of the user, including but not limited to head movements, walking behavior, degree of consciousness, and distraction.

It is understood that an "accelerometer" may be realized as one or more accelerometers, gyroscopes, magnetometers, or the like, as well as combinations thereof.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. Throughout the drawings, like-referenced characters are used to designate like elements.

In the drawings:

FIG. 6A is a schematic drawing showing an arrangement enabling simultaneous capturing of images of both eyes of the user, according to an embodiment of the present invention;

FIG. 6B is a schematic drawing of a portion of the first optical path of the arrangement of FIG. 6A;

FIG. 7G provides a perspective view of a headset frame having a rear cover and containing an adaptor arrangement;

FIG. 8 is a schematic drawing of a headset viewing assembly having an illumination arrangement;

FIG. 8A provides a schematic top cross-sectional view of a portion of headset viewing assembly in which the illumination arrangement includes a diffuser plate;

DESCRIPTION OF SPECIFIC EMBODIMENTS OF THE INVENTION

Figure 1C:
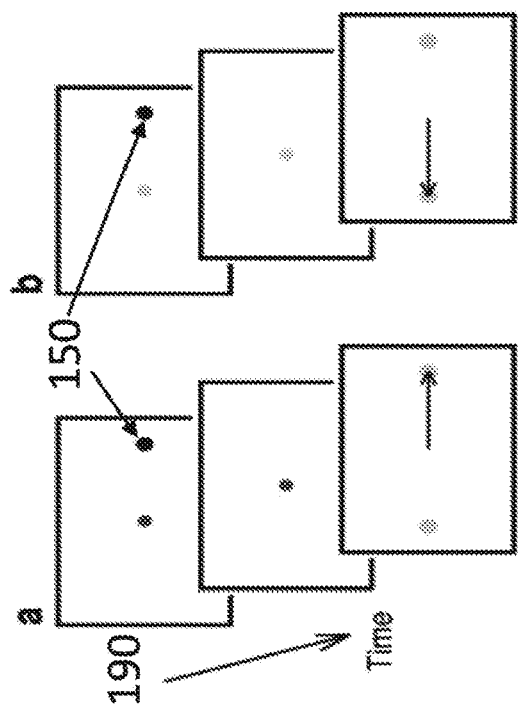
FIG. 1C provides a schematic view of a series of stimuli displayed, over time, to the eyes of the patient by the inventive headset apparatus.

The principles and operation of the apparatus and methods of the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The present invention, in some embodiments, relates to methods and devices for generating and applying a modifiable protocol for a patient with a vestibular or other relevant medical impairment. In some embodiments of the invention, a headset of goggles may be applied to a patient to allow for presentation of stimuli and recordation of performance behavior. The methods herein described can, in some embodiments, be customized for specific patient needs, progress, or developments.

A first aspect of the present invention is a system including a computer or computational device, at least one software application on the device or external thereto (e.g., a cloud-based application), a communication protocol, a virtual reality or augmented reality helmet or goggles or a flat panel display, a head, eye and body tracking device or devices, a stimulus generating system, and a real time visualization tool.

Figure 1B:
FIG. 1B provides a perspective view of a mobile phone having a camera, for use within the apparatus of FIG. 1A.
Figure 1A:
FIG. 1A provides a perspective view of a headset apparatus according to an aspect of the present invention.

FIG. 1A provides a perspective view of a headset or headset apparatus 105 according to an aspect of the present invention, the headset adapted to be donned and used by a general user (e.g., for gaming, social media, marketing), or by a patient or user having a vestibular impairment (e.g., due to a previous illness).

With reference now to FIGS. 1A and 1B, headset 105 may include a case or goggle case (or rear cover) 107 adapted to accept a mobile computing device 120 (typically a mobile phone) having a display screen 115 such as a multi-touch screen, such that when headset 105 is worn by the user in a donning mode, mobile computing device 120 faces the eyes of the user. Case 107 is optionally removable. Headset 105 typically includes a headband or similar means for holding or securing the apparatus on the head.

It will be appreciated by those of skill in the art that case 107 may be further adapted to accept any one of various mobile computing devices having different geometries. A mobile computing device 120 according to the instant invention may advantageously include a computer processor, at least one camera, and a display screen. More typically, mobile computing device 120 may further include a wireless connectivity function, speaker, microphone, and at least one accelerometer. A camera or camera lens 110 of mobile computing device 120 is adapted to face the user.

An optical element or arrangement 130, disposed within headset 105, may be adapted to focus the eyes of user on camera 110. In some embodiments this is realized by means of a smartphone or similar mobile communication/computing device. It will be appreciated by those of skill in the art that optical arrangement 130 may include at least one mirror as well as any other elements that allow the eyes to be in focus for camera 110 of mobile computing device 120. The optical arrangement may be attached to headset 105 substantially as shown. Mobile computing device 120 may include a second camera (not shown) facing away from the user, and may be adapted to video the surroundings and to present the surroundings to the user so as to add an element of augmented reality to exercises performed by the user. Referring now to FIG. 1C as well, mobile computing device 120 may be adapted to include and run at least one application for providing stimuli 150 within a successive series of frames a and a series of frames b, series of frames a being displayed to the left eye of the user, successive series of frames b being displayed to the right eye of the user, over time, the progression being denoted by arrow 190. In one example of the stimuli movement, an object is presented to the user. This object moves in the virtual world and is seen by means of the screen. The movement in the virtual world is presented though a set of frames where the object is moving (changing position) in successive frames. When the same image is presented to each eye, the stimulus is seen in two dimensions. When each eye receives a different stimulus, depending on the relative position of the eye to the object, the object is perceived as three-dimensional.

The application may be further adapted to store, analyze, transmit and present results from exercises performed by the user. User eye and head movements may be measured/monitored by at least one accelerometer typically disposed within mobile computing device 120, while speakers associated with the mobile computing device may provide real-time feedback and/or deliver performance information to a non-patient observer or medical care provider.

The system may be adapted to provide visual stimulation that unleashes specific eye movements and head movements that produce dizziness, so as to train the brain to output a suitable vestibular-ocular response. There is also an interaction with the body to combine body-head-eye movements that promotes compensation mechanisms of the brain when some such movements provoke dizziness. The stimulation may replicate already established exercises such as vestibular rehabilitation therapy, (VRT) and aims at unleashing neuroplasticity mechanisms (compensation, substitution and habituation). The same principles may be applied to train eye movements in several different eye pathologies as well.

This system may be extended to incorporate gait analysis while a user is being subjected to visual, vestibular, proprioceptive or/and auditory stimulation.

In some embodiments, the system includes a tablet and a pair of virtual reality goggles having a head tracking system.

The user's device is loaded with a training protocol that the user uses as indicated by a suitable clinician (e.g., a physical therapist. By way of example, the protocol may include operating the system twice a day, for 20 minutes each time). Data from the usage is collected and automatically stored in the device. Data may be sent wirelessly to the therapists or by a wired connection on the next appointment. This way the therapists can track and check the correct use of the system. The therapist may utilize a different program that allows for the storing of all information and creating or editing the exercise protocol.

It will be appreciated that various platforms for virtual reality using mobile devices are commercially available, including: Google Cardboard (Google); Pinc (developed by Cordon); VR One (Carl Zeiss); Samsung Gear VR (Samsung Gear); vrAse (vrAse); and DuroVis (DuroVis).

The stimulus generating system may produce at least one of the following types of stimulation:

saccadic (2D and 3D)—horizontal, vertical, and random, with or without 3D depth, to train quick eye movements; successive saccadic stimulation may be similarly effected, but with successive small saccades defining an eye trajectory, while saccades become less frequent to achieve one large saccade, or by varying the time to achieve the next saccade.

retinal optokinetic stimulation—a flow of objects inside a scene that covers the whole retina.

foveal optokinetic stimulation—a flow of defined objects. The object of interest must be positioned in the fovea, the area of the eye that is able to see details.

retinal vestibular-visual stimulation—a stimulation that resembles retinal optokinetic stimulation, but also includes head movements that adjust the point of view in the virtual world.

foveal vestibular-visual stimulation—analogous to retinal vestibular-visual stimulation, in which the object of interest must be positioned in the fovea.

real life locations with superimposed stimulation—scenes of commonly used rooms and environments where the stimulation is superimposed.

head movement exercises—while being immersed in a virtual reality scene, the subject is instructed to search for a specific object. To perform the search and explore the scene, head movements are required. When the object is found (e.g., a visual mark is placed over the object), the exercise is over. Information is obtained from an analysis of the movements.

Figure 2:
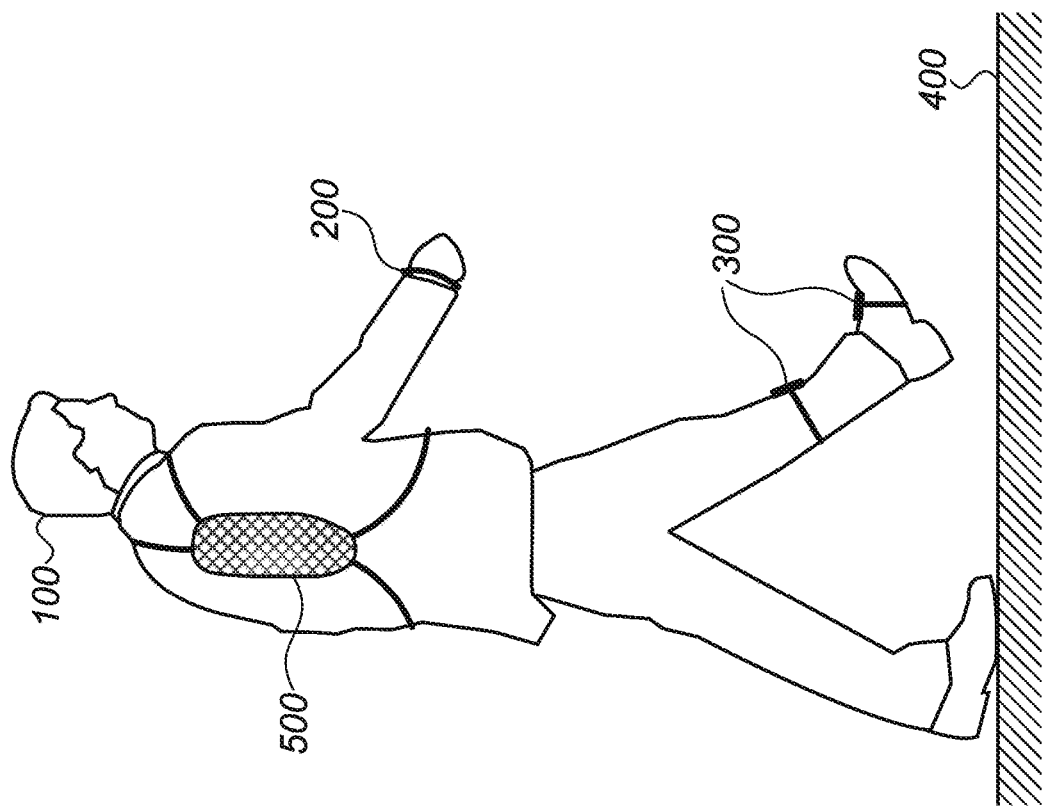
FIG. 2 provides a gait measuring and analysis system that combines body tracking with sensory stimulation, according to an aspect of the present invention.

Referring again to the drawings, FIG. 2 provides a gait measuring and analysis system, according to an aspect of the present invention. The system may challenge the balance system by sensory stimulation. The brain is challenged by different type of sensory stimulation to produce the correct output (e.g., oculomotor and spinal). Different types of stimulation will produce a challenge that, depending on the brain's capacity, will be resolved at certain degree. When the same output is measured under different sensory conditions or sensory stimulation, the capacity of the brain to resolve under those conditions is assessed.

In one exemplary embodiment, a subject dons a pair of virtual reality goggles 100 connected to, or associated with, a stimulus generator device 500 and wearing body tracking accelerometers disposed on the body of the subject, such as leg-mounted accelerometers 300 or wrist-band accelerometers 200. The subject is instructed to walk while the body tracking system records movement and visual stimulation is presented. Real time analysis of the parameters can be used to adjust the stimulation. Further processing determines gait parameters such as cadence, step length, speed, etc., that can be compared to the same set of parameters under different sensory conditions. This may be extended or applied to any type of movement or exercise, any body tracking system and vestibular, proprioceptive and/or auditory stimulation. Visual stimulation may be presented by means of virtual reality goggles (virtual reality or augmented reality); vestibular stimulation by commanding head movements; proprioceptive stimulation by adjusting the surface where the exercises are executed; and auditory stimulation by means of headphones or loudspeakers. The walking surface may be a firm floor or other surface 400 that alters proprioceptive information.

Another embodiment of the invention may include the previous described embodiment where the walking surface is a walking floor mat that has a tilting mechanism adapted to produce an inclination in at least a portion of the mat. The mat is also capable of recording foot pressure. The combination of a Sensory Organization Test (SOT) with gait analysis extends SOT from standing to walking. Balance impairment may be determined by providing sensory stimulation according to a moving pattern of the walking surface. In one exemplary embodiment of the invention, a subject is instructed to walk along a floor mat that senses foot pressure under different sensory conditions. These may include:

eyes closed, firm surface;
eyes open, firm surface;
wearing virtual reality goggles that present stimulation according to the pressure distribution under the feet;
eyes closed, moving surface;
eyes open, moving surface;
wearing virtual reality goggles presenting varying stimulation depending upon the pressure distribution under the feet. The standing surface measures different oscillations of the body sway. The distribution of the body weight under the feet varies due to these oscillations. This distribution can be measured and used to alter the visual stimulation.

SOT is a form of posturography that assess the ability to use visual, proprioceptive and vestibular cues. In the present embodiment, instead of measuring the center of pressure during quiet stance and setting the visual or surface inclination, the information is now used to move the surface on which the subject is walking. The pressure profile during walk is used to determine a virtual center of pressure that is used to modify the display on the virtual reality goggles or/and the inclination of the floor mat.

Information from all tests described above, combined with a permanent body tracking system (such as body tracking accelerometers 200 or 300) can be used to analyze the evolution during the rehabilitation process. During a rehabilitation process, quiet stance, gait parameters and questionnaires are expected to show the evolution of the subject performing the rehabilitation. However, continuous monitoring of the subject generates a significant amount of data that can be correlated with specific patterns of the recorded data. This method can be used to provide metrics to the evolution of the rehabilitation therapy and in long term use, may provide information to correlate the data patterns with specific events (falls, dizziness, etc.) when compared to the subject's own historical data or data collected with respect other subjects.

Monitoring Activities of Daily Living and Assessment of Body Movements

An important element of the rehabilitation is to determine the activities of daily living, since these are an indicator of functional status. Such activities can be tracked by means of sensors worn on the body. FIG. 2 shows an example of such sensors disposed on a wristband or disposed on the legs. Traditional methods for functional assessment of the balance system are based on periodic clinical evaluations. These evaluations test the different systems involved in balance such as eye movements and postural control. Examples include VNG and posturography. These evaluations are discrete assessments that give a picture of patient performance in a clinic environment.

In one embodiment of the present invention, the assessment is extended to a continuous evaluation during the time in which the patient exercises. This assessment is aiming at adapting the stimulation based on patient performance, in real time.

Ultimately, the improvement in quality of life (identified in this case as an increase in daily activities as measured by the sensors) is the objective of the rehabilitation process. The information derived from monitoring patients during the days or weeks in which they perform rehabilitation exercises, is fed into the Initialization of the Parameters of the rehabilitation stimulation as an additional input. The information about daily activities is also available to the therapist to determine the impact of the treatment on daily activities, and complements the traditional measurements that tend to more focus on the response of the different systems involved (e.g., oculomotor response).

Assessment of Body Movements

As an extension to the classic posturography, the inventors have discovered that several other body activities can be performed while being subject to different visual, auditory or proprioceptive stimulation. A patient can be instructed to walk in a straight line while different stimulation is presented. This allows to measure the patient's response to different sensory stimulations under the same body activity. It also allows to compare the results under one type of stimulation and one body activity to patient cohorts. This can be seen as an extension to posturography (standing on a platform under different sensory conditions) and as extension to gait analysis (walking along a mattress with sensors, without changing the sensory conditions). The inventors have discovered that a combination of both approaches, namely, tracking body movements (e.g., gate analysis) while providing sensory stimulation (e.g., visual) provides more and richer information and a more complete functional assessment of the balance system than those attained by traditional methods.

Figure 3:
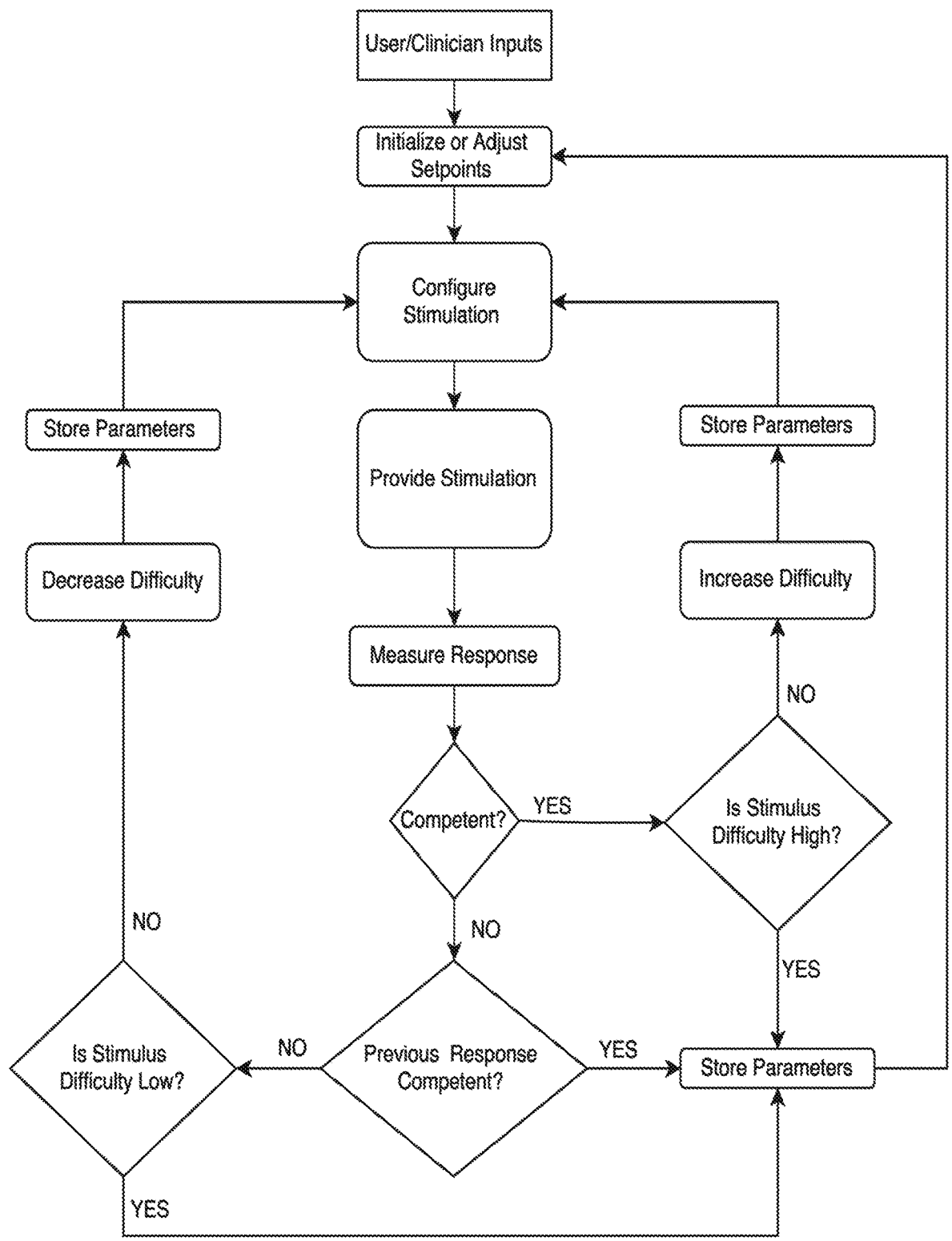
FIG. 3 presents a procedure to determine the threshold of competence for a stimulation, and to generate and deliver successive stimulations.

FIG. 3 presents a procedure to determine the threshold of competence for a stimulation, and to generate and deliver successive stimulations.

The procedure may begin with initialization of setpoints for the particular stimulation procedure being implemented. These setpoints, which may pertain to parameters such as the velocity, size, or frequency of the stimulation, are used to configure the stimulation exercise. The setpoints may also be influenced by user and/or clinician inputs. For example, the system processor may prompt the clinician to rate a particular condition of the patient on a scale of 1 to 5, and subsequently adjust the setpoints accordingly. Similarly, the patient may be prompted to rate various particular patient conditions, e.g., pertaining to mood, alertness, tiredness of the eyes, and headache severity, and based on the input, the system processor may accordingly adjust the setpoints.

The clinician input can also include results from other tests. For example, the clinician may incorporate one of the following:

caloric tests results according to the percentage of asymmetry in the response.

misidentification of the target, tested by increasing velocity of saccades or smooth pursuit while identifying an icon until the icon is misidentified certain percentage of the times.

adjustment of the icon size depending on the automatic dynamic visual acuity test (ADVA).

VNG Results, while using the gain deficit in smooth pursuit, saccades and optokinetic nystagmus to select the exercise and parameters of the stimulation (such as velocity or direction).

sensory organization test (SOT) results. The SOT is a gold standard test that aims at identifying the source of a balance disorder. The outcome of the test will provide information on the contribution of the vestibular, proprioceptive or visual system to the patient's condition. The output of the test can be used to feed our system when producing protocols.

pathology or diagnosis, such as a vestibular or central disorder. The clinician may also specify a non-specific condition such as with respect to elderly population.

Once the stimulation has been configured, the stimulation is administered to the user, for example, a smooth pursuit stimulation, in which the object is a sphere, as shown in FIG. 1C, using the apparatus described with respect to FIGS. 1A and 1B.

The system is adapted to track at least one of the eye movement and the head movement of the user, typically both types of movement, using the on-board camera and accelerometers. Thus, the response of the user to the stimulation is measured or quantitatively determined, instead of relying upon a verbal response from the patient, which couples cognitive issues into the assessment of competence.

Subsequently, the system processor determines the competence of the user response. The determination of user competence includes a comparison between the expected response to the actual response of the user to the stimulation provided. Each type of stimulation may target a different oculomotor response or reflex. In the ideal case, the difference (delta) between the expected response and actual response may tend to zero. In some cases, the expected result is simply the presence of a particular eye movement, while in other cases the existence of the response is complemented with a certain velocity, rate or gain. In the case of a smooth pursuit stimulation, which is a velocity servosystem that allows placing on the fovea an object typically moving at speeds of up to 30 degrees per second, competence is determined if at such speeds, the eyes can gradually follow the object, or whether a corrective quick eye movement is necessary to reach the target. When saccadic stimulation is provided to the patient, competence of the user response is determined by measuring movements that may to some degree overreach or underreach the target. Vestibular ocular reflexes (VOR) are tested by comparing the head and eye movements and determining the degree to which the gain of the movement (head velocity/eye velocity) is close to 1. For various other types of stimulation, the existence of the response may already indicate competence, for example, in optokinetic stimulation, in which the presence of nystagmus is expected.

If the system processor determines the response of the user to be competent, the processor may then increase the difficulty of the stimulation (e.g., by increasing the velocity of the stimulus) for the next session, for the next exercise within the current session, or for the continuation of the current exercise. The parameters may then be stored, and the stimulation is reconfigured.

Optionally, if the system processor determines the response of the user to be competent, the processor may check whether the stimulus difficulty is high (e.g., above a preset value pertaining to a personal or group nom), in which case the stimulus difficulty may be maintained.

If the system processor determines the response of the user to be incompetent, the processor may then decrease the difficulty of the stimulation (e.g., by decreasing the velocity of the stimulus) for the next session, for the next exercise within the current session, or for the continuation of the current exercise. The parameters may then be stored, and the stimulation is reconfigured.

Optionally, if the system processor determines that the previous response of the user was also incompetent, the processor may maintain the stimulation at the current level of difficulty.

Another example where competence is assessed involves a head movements exercise. In this case, a special parameter of interest involves a comparison between the shortest path to the object and the required path. Another special parameter is the velocity of the head movements. In a more general sense, several parameters can be derived from the head movements to compare them to the shortest path to the target. This stimulation can be extended to include eye tracking to compare the actual trajectory of the eyes to the shortest path to find the target. The stimulation described above may include head and eye tracking to compare expected movement to actual movement. This information can be compared with the results of previous exercises (studying the evolution of the response) or to the performance of others (e.g., nonnative performance). The performance of others may be derived from a normal range or from a range specific for a particular pathology.

In stimulation intended to unleash the ocular movement (e.g., smooth pursuit, saccades, nystagmus and interaction between visual and vestibular systems) using virtual reality, it may be difficult to verify that the stimulation is actually unleashing the expected movement. In order to solve this, some previous approaches have included, in the stimulation, an icon (letters or numbers) that the patient needs to identify, and then enunciate, so that the therapist can verify that the ocular movement is being performed correctly.

The inventors have discovered that stimulation involving the identification of letters or icons targeted at verifying compliance with an exercise, require a second cognitive task that may disadvantageously produce both false positives and false negatives. Subjects may correctly identify the icon, but may have difficulty with the enunciation, due to a variety of factors unrelated to functional competence of the oculomotor system. Subjects may guess the icon based on partial identification. For example: the digits 3, 6, 8 and 9 may be guessed on the basis of similar shapes. False negatives may be attributed to a variety of causes, including lack of attention, cognitive impairment, lack of concentration, visual impairment, decreased acuity and even the effort to produce speech.

The inventors have further discovered that that in order to better assess the functional competence of an oculomotor system (e.g., smooth pursuit), such cognitive tasks may be eliminate or substantially reduced such that the focus may be placed solely on the oculomotor response. By tracking stimuli that target the basics of the oculomotor systems, the online adjustments of the stimulation based on the performance of the subjects may largely eliminate false positives and negatives, thus achieving a more "pure" analysis of the oculomotor system involved.

Figure 4:
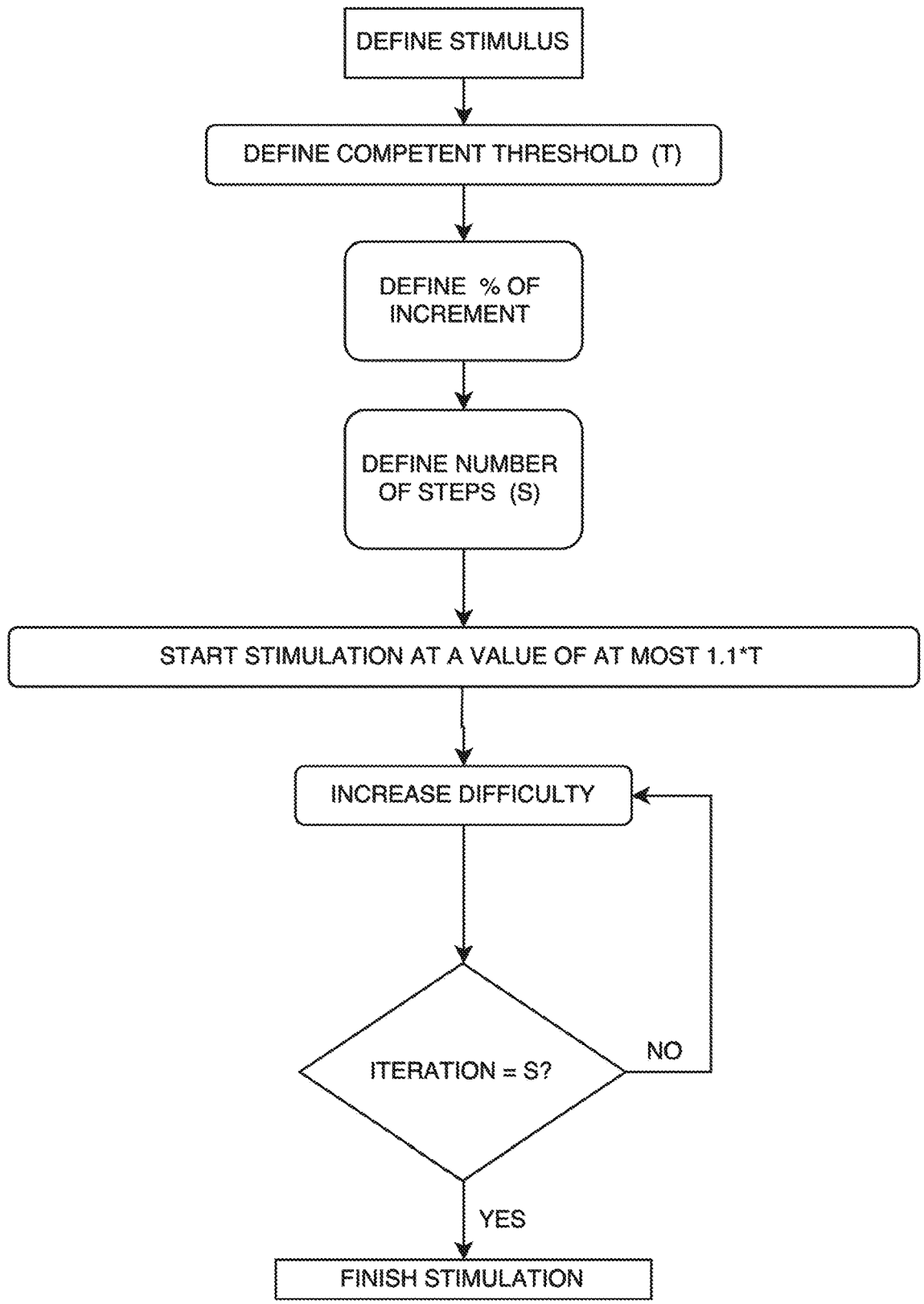
FIG. 4 describes a procedure to generate and deliver successive stimulation in which the level of difficulty is increased around a determined threshold, according to another aspect of the present invention.

FIG. 4 describes a procedure to generate and deliver successive stimulation in which the level of difficulty is increased around a determined threshold, according to another aspect of the present invention. The procedure includes defining a stimulus, providing the stimulus to the patient, measuring the patient response while varying at least one parameter of the stimulus. By way of example, when presenting a stimulus to train smooth pursuit, the velocity of the object is varied until the response is no longer competent. At this point, the threshold of competence is determined. Two more elements may need to be defined: (1) the percentage of increment, which indicates how much the threshold will be surpassed, and (2) the number of steps required to reach the increment. The exercise starts at an initial velocity and is increased based on the elements defined, until the requisite number of iterations is reached.

Specifically, if the intention is to reach 5% above the velocity threshold in 10 steps, the stimulus can be configured to start at 5% below the threshold and increase velocity in each step by 1%. Alternatively, the stimulation can start at the threshold level and increase the velocity 20% above the threshold in two steps. In one example, a smooth pursuit stimulation is determined to be competent at 20 degrees/second, a stimulation is set to start at 21 degrees/second, increasing 5 times in steps of two degrees/second, until reaching 31 degrees/second.

When the number of steps is reached, the process is over.

Another example is to present a saccadic stimulation and subsequently determine user response competence. This competence can represent the maximum velocity that the saccade can have until successive corrective saccades appear to compensate. The stimulation may be provided in several steps, so as to increase the length of the saccade until a certain number of iterations is reached. For example, a saccade competence can be determined to be 100 degrees/second. A stimulus to train this saccadic reflex is set to start at 90 degrees/second and increase in 10 steps of 5 degrees/second (generating longer saccades). In such a case, the first saccade may be at 90 degrees/second, the second saccade may be at 95 degrees/second, until a tenth saccade is presented at 140 degrees/second.

The system may be adapted and configured to track eye movements during stimulus presentation, determine the parameters to be used (e.g., velocity) based on the most challenging parameter in which the brain continues to maintain competency (e.g., in smooth pursuit, when a corrective saccade is required). The system may be adapted and configured to perform a progressive increase of a particular therapeutic parameter from minus delta to plus delta around the point of discontinuity. For example, when a patient is presented with a smooth pursuit stimulation and the velocity of the stimulus is too high, the patient will perform a corrective saccade (i.e., a quick eye movement to continue looking at the point of interest). The velocity where the smooth pursuit is not competent is set as a threshold and the proposed stimulus implies increasing the velocity of the stimulus from a value below competence to a higher value, typically above competence. Another description includes presenting a certain stimulus, determining competence at the exercise and setting the parameters according to the results, for example, setting the velocity of the stimulus based on the threshold determined. Another example is presenting a certain stimulus, determining competence at the exercise and setting the challenging parameter to increase during the same exercise from below competence to above competence. The velocity increments can be configured to increase along a certain period of time (days, weeks), not necessarily during the same session. For example, if the brain is not competent to perform saccades above 10 degrees/second of eye movement, the training could be done using saccades that start at about 6 degrees/second eye movement and increase until 14 degrees/second of eye movement.

The system may send data over a network and receive instructions over a network. The information collected about the usage of the system is uploaded to a central server for remote review. The therapist can update the protocol and send the new version over a network.

The apparatus and methods of the present invention may also be applied to various oculomotor treatments, including poor binocular coordination, convergence insufficiency, amblyopia, diplopia, strabismus, stress-related visual problems, visual rehabilitation, TBI, stroke, whiplash, development delays, and Brock string-like exercises.

In another exemplary embodiment of the invention, a pair of augmented reality goggles may be used to superimpose the stimulation onto the actual environment that the patient or subject is present.

Figure 5A:
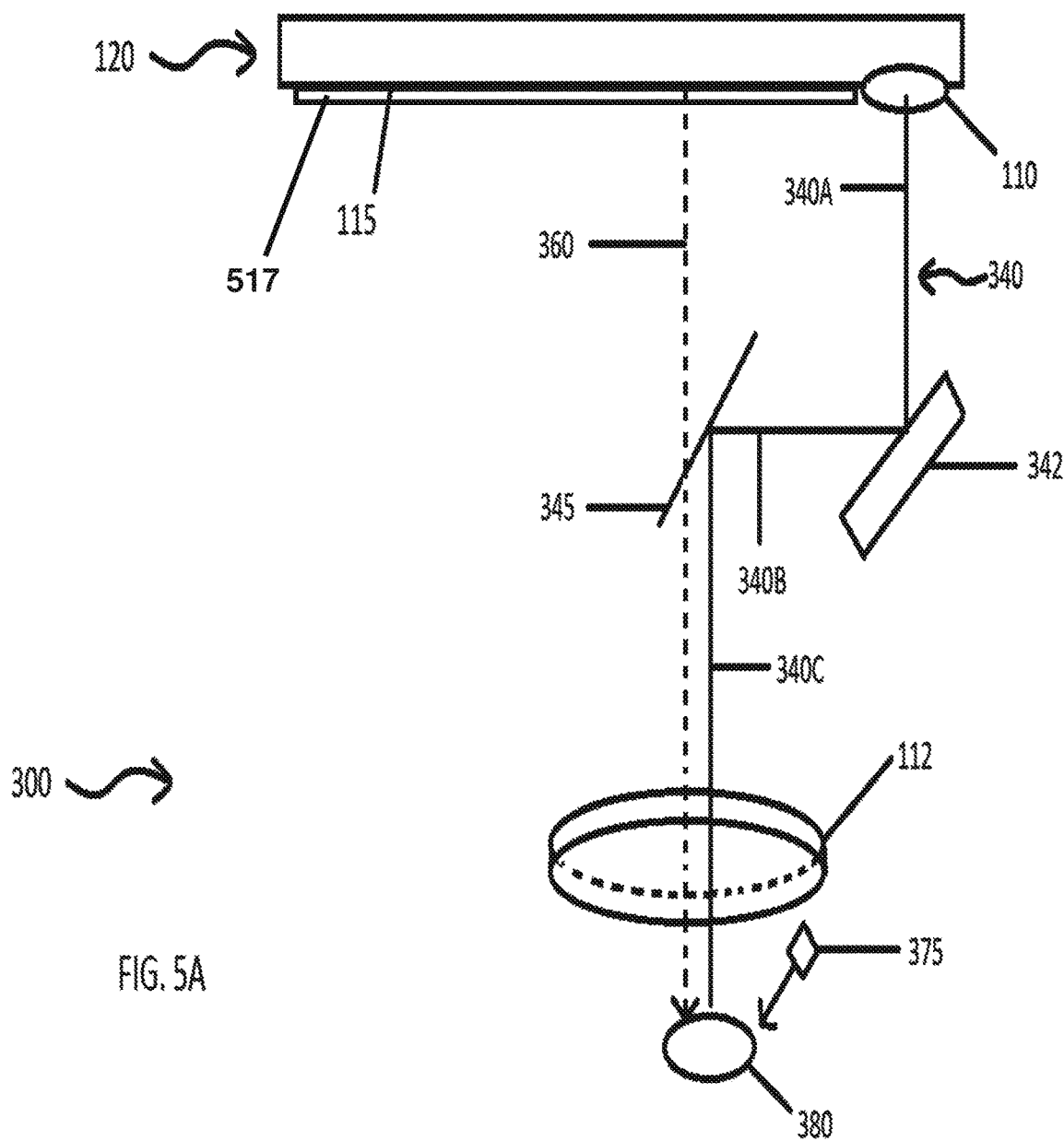
FIG. 5A is a schematic drawing showing the first and second optical paths within the viewing arrangement, according to the present invention.

FIG. 5A is a schematic drawing showing a first optical path 340 and a second optical path 360 within a viewing arrangement or apparatus 300, according to the present invention. The eye 380 of the user views an image displayed by display screen 115 of mobile computing device 120 via second optical path 360. Second optical path 360 includes at least one optical splitter such as beamsplitter 345, and a viewing lens 112.

First optical path 340 may be directed from eye 380 of the user, via viewing lens 112 to at least one optical splitter such as beamsplitter 345. This first section of first optical path 340 is labeled 340C. In a second section 340B of first optical path 340, a portion of the incident light is reflected by the optical splitter towards at least one optical angle modifier 342. In some instances, at least one optical angle modifier or optical angle modifier arrangement 342 may include two or more optical angle modifiers disposed in series.

From the ultimate unit of optical angle modifier 342, the light is directed towards camera lens 110 of mobile computing device 120. This third section of first optical path 340 is labeled 340A.

In some embodiments, a light source 375 may be positioned to direct light at eye 380 of the user. This light source may include visible light and/or infra-red light.

In some embodiments, the optical splitter may include a hot mirror, for use with infra-red light.

In reducing the invention to practice, the inventors have found that a portion of the light emitted from display screen 115 is directed to mirror 342 and from there, to camera 110. This light may be disadvantageous, generating noise for the image received by camera 110, whose purpose is to get an image of eye 380 using beam splitter 345. The inventors have further found the magnitude of this disturbance to be significant.

The inventors have discovered that a screen filter 517 may be placed near and preferably so as to touch screen 115. Screen filter 517 may advantageously be adapted to block or largely block low-angle emitted light (e.g., at most 50°, at most 40°, at most 30°, or at most 20°), such that only light rays having a high angle (e.g., at least 20°, at least 30°, at least 40°, or at least 50°), with respect to screen 115, pass through filter 517. Since the apparatus is adapted such that eye 380 views the screen at an angle of substantially 90°, the entire screen is viewable, screen filter 517 notwithstanding. Mirror 342, however, is positioned and angled with respect to screen 115, such that screen 115 is viewed by camera 110 as a black or substantially black surface.

By way of example, screen filter 517 may be, or include, a privacy screen filter or privacy screen filter or protector that is a 2-directional filter such as a 3M™ Privacy Screen Protector. Such a filter may or may not have an adherent broad surface.

In some embodiments, screen filter 517 may be adhered to screen 115, but in a generally perpendicular fashion with respect to the normal direction of adherence for such screen filters (i.e., such that the filtering is towards the top and bottom of the mobile unit or cellular phone.

The apparatus may include an (opaque) internal separator (typically generally perpendicular to the screen and generally parallel to the line of sight of the eye 380) adapted to provide each eye with an optically isolated viewing chamber, as described further in detail hereinbelow, with respect to FIGS. 10A and 10B. Such an internal separator may be operative for all embodiments of the present invention.

Beam splitter 345, besides providing an image from eye 380 by reflection, further—disadvantageously—may provide an image of the separator, partition, or wall by transparency. The inventors have discovered that by utilizing the above-described screen filter, and by utilizing a dark (typically black) and preferably non-reflective surface for the separator or partition wall (by way of example, separation wall 1098 in FIGS. 10A and 10B), a pane of glass (e.g., regular or window glass) may be used for beam splitter 345.

Glass having smooth viewing surfaces reflects a portion of the incident light, such that in practice, the glass behaves as a beam splitter. Preferably, the glass pane or element should be selected and/or adapted to reflect at least 2% or 3% of the incident light, and more typically, at least 4%, at least 5%, or at least 6%, of the incident light. Typically, such a glass pane or element may reflect the incident light within a range of 2-80%, 2-60%, 2-40%, 2-30%, 2-20%, 2-15%, 2-10%, 4-40%, 4-30%, 4-20%, 6-40%, 6-30%, or 6-20%. It must be emphasized that since glasses may be prepared from different materials, and in different manners, the range of the extent of the reflection is broad, from 100%, if coated with a mirror, or close to 0%, if provided with an antireflection coating.

The beamsplitter may also be made from glass, e.g., having a partially reflective coating. The beamsplitter may also be made from various transparent plastics.

Figure 5B:
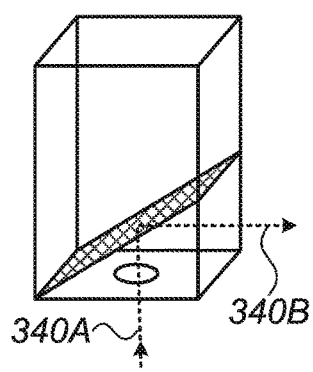
FIG. 5B is a schematic drawing of an exemplary optical angle modifier for use in conjunction with the present invention.

FIG. 5B is a schematic drawing of an exemplary optical angle modifier 342 for use in conjunction with the present invention. Optical angle modifier 342 may typically include a mirror. Other technological alternatives will be readily apparent to those of skill in the art.

FIG. 6A is a schematic drawing showing an optical arrangement 600 enabling simultaneous capturing of images of both eyes of the user, according to an embodiment of the present invention. First optical path 340 is directed towards a first optical angle modifier 342A, whose output light or line of sight is directed towards a second or ultimate optical angle modifier 342B. First and second optical angle modifiers 342A, 342B are adapted and positioned within arrangement 600 such that the output light or line of sight from the second or ultimate optical angle modifier 342B is directed or largely directed towards a pair of optical splitters such as beamsplitters 345A, 345B. A portion of the incident light is directed by beamsplitter 345A to a first eye (not shown) of the user, and a portion of the incident light is directed by beamsplitter 345B to a second eye (not shown) of the user.

FIG. 6B is a schematic drawing of a portion of first optical path 340 of the arrangement 600 of FIG. 6A. It may be observed that the field of view of the camera lens (not shown) sustained via first optical angle modifier 342A broadens as function of distance along the optical path.

Figure 7C:
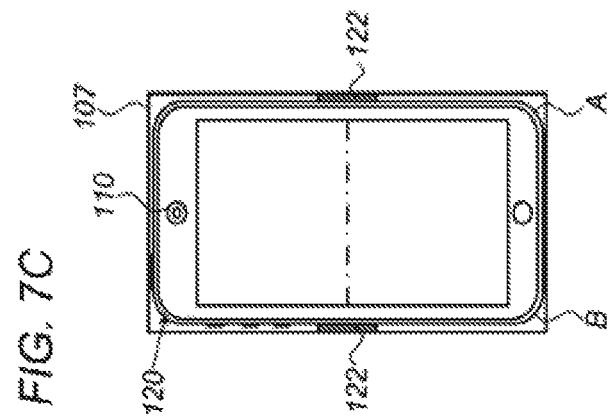
FIG. 7C is a schematic drawing of a holding case forming a component of the viewing apparatus according to one aspect of the present invention.
Figure 7B:
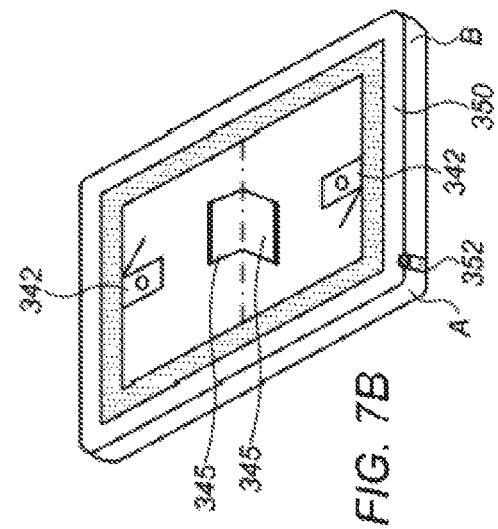
FIG. 7B is a schematic drawing of a monolithic optical adapting arrangement according to one aspect of the present invention.
Figure 7A:
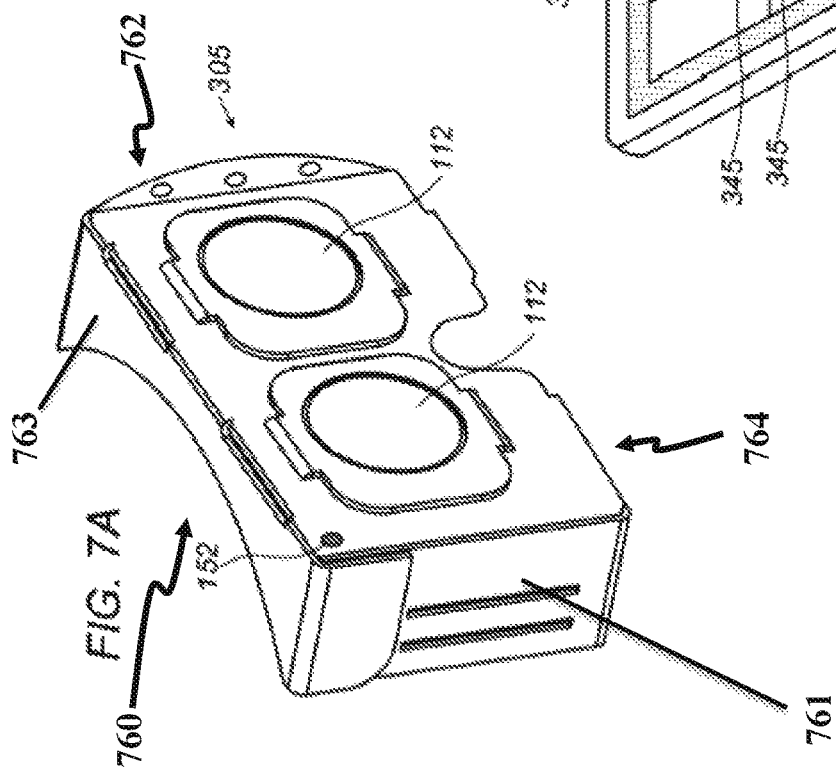
FIG. 7A is a schematic drawing of a headset viewing assembly forming a component of the viewing apparatus according to one aspect of the present invention.

With collective reference now to FIGS. 7A-7C, FIGS. 7A-7C are schematic drawings of components of a viewing apparatus according to aspects of the present invention. FIG. 7A is a schematic drawing of a headset viewing assembly 305 having a pair of headset viewing lenses 112. Viewing lenses 112 may be optically adapted to reduce the focal length of the eyes viewing therethrough. FIG. 7B is a schematic drawing of an inventive monolithic optical adapting arrangement 350. FIG. 7C is a schematic drawing of a mobile phone holding case or rear cover 107 of the viewing apparatus. For the sake of clarity, the figures are provided with identification letters A and B, which represent alignment indicators for the three components (i.e., points A of each component align, as do points B of each component). Together, headset viewing assembly 305, monolithic optical adapting arrangement 350, and holding case or rear cover 107 (along with an optional headgear for suitably holding the components onto the head, such that the eyes of the user are fixed in place to view via headset viewing lenses 112) may form a complete headset apparatus.

Headset viewing assembly 305 includes a viewing recess 760, which is designed and dimensioned to enable a user to juxtapose his face thereto, such that eyes 380 can suitably view a target via viewing lenses 112. Viewing recess 760 may be enveloped by a wall or at least one wall, and in the embodiment of FIG. 7A, by side walls 761 and 762, and by top and bottom walls 763 and 764.

As shown, holding case or rear cover 107 includes a holding mechanism 122 (e.g., spring-loaded) adapted to secure mobile computing device 120 in a fixed position. Holding case 107 may be secured to headset 305 in various ways known to those of skill in the art. Most typically, holding case 107 is secured to headset 305 by sliding the case into a complementary recess in the headset, as may be seen in FIG. 1A.

Monolithic optical adapting arrangement 350 may be secured to headset 305 by a fastener 352. Fastener 352 may form a portion of a fastening arrangement along with a fastener or complementary fastener 152 in headset 305. Such fastening arrangements may include, but are not limited to, hook and loop arrangements, screw and screwhole, clasp arrangements, pressure fit or snap fit arrangements, etc.

Figure 7D:
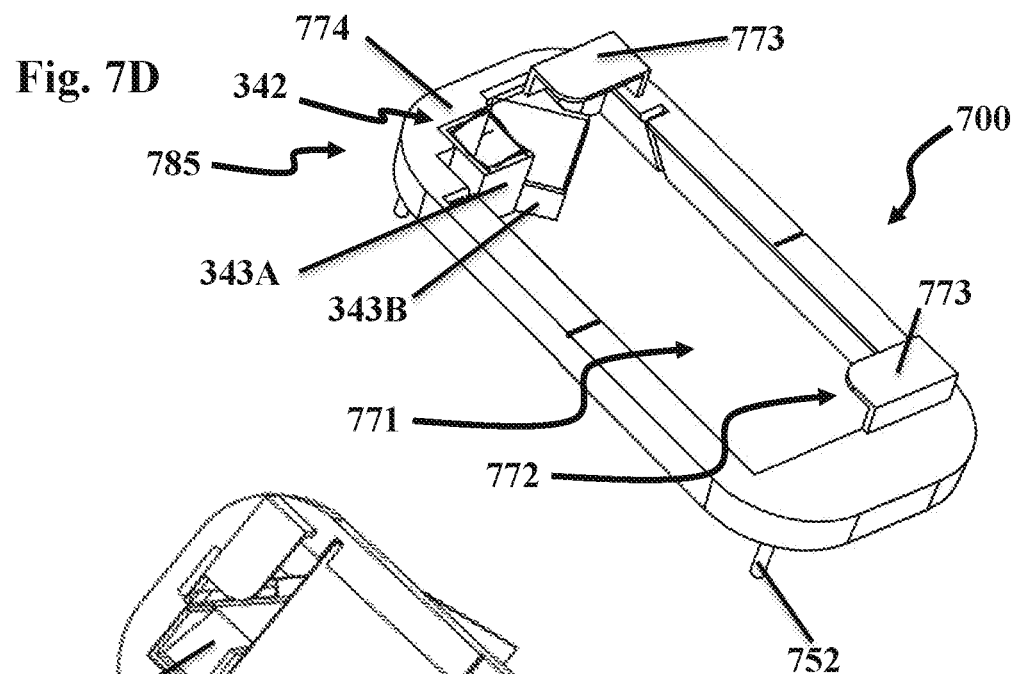
FIGS. 7D-7F provide perspective views of an exemplary adaptor arrangement for adapting the size and camera position of a particular mobile computing device to the headset apparatus, according to aspects of the present invention.
Figure 7E:
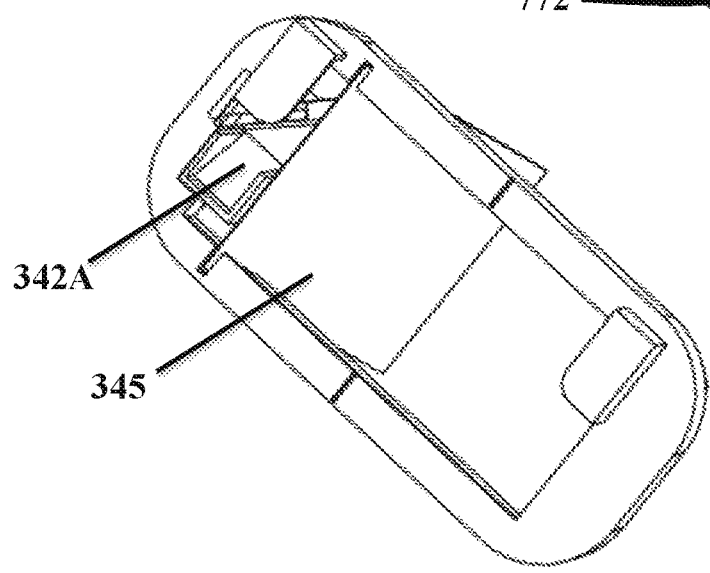
Figure 7F:
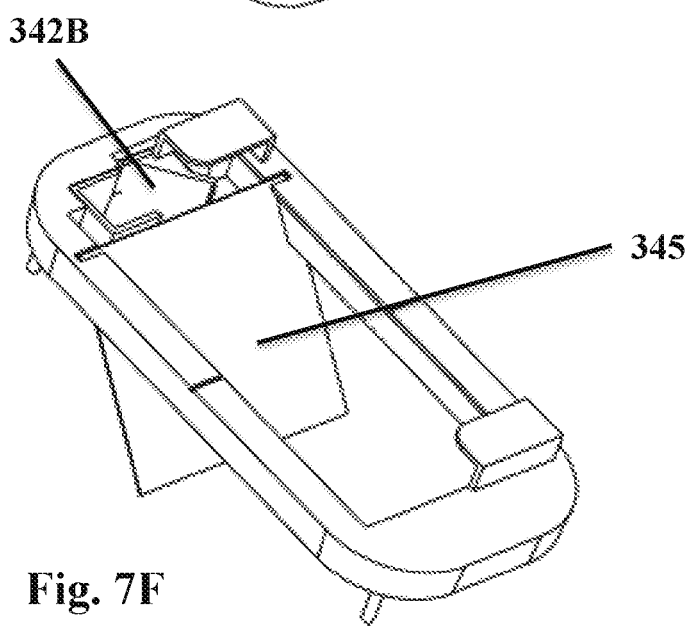

With collective reference now to FIGS. 7D-7F, FIGS. 7D-7F provide various perspective views of an exemplary adaptor arrangement or holding case 700 for adapting the size and camera position of a particular mobile computing device 120 ("cellphone", not shown) to the headset apparatus, according to aspects of the present invention. Thus, a plurality of such dedicated adaptor arrangements 700 may be produced, each dedicated to the dimensions and/or camera position of one or more particular cellphones.

Adaptor arrangement 700 may include a cellphone receiving arrangement 771, which may include a recess or slot for receiving the cellphone. In exemplary adaptor arrangement 700, receiving arrangement 771 includes a slot 772 formed by one or more cellphone guiding elements or guiding corners 773. The cellphone may be placed on a broad face 774 of adaptor arrangement 700, and slid into slot 772. Cellphone receiving arrangement 771, alone or in conjunction with other components of the headset, may deterministically orient and/or position the cellphone into the proper position, such that the camera on the cellphone screen is optically aligned with on-board optical arrangement 785.

Typically, on-board optical arrangement 785 includes at least one optical angle modifier or optical angle modifier arrangement 342, which is adapted and positioned to direct light between or second section 340B of first optical path 340 (shown in FIG. 5A) to camera lens 110 of the cellphone, when the cellphone is in place in adaptor arrangement 700.

Optical angle modifier arrangement 342 may include one or more optical angle modifiers. In the exemplary embodiment provided in FIGS. 7D-7F, optical angle modifier arrangement 342 includes first and second optical angle modifiers 342A, 342B, which are adapted and positioned to direct light from a beamsplitter such as (onboard) beamsplitter 345, to camera lens 110 of the cellphone.

Figure 10A:
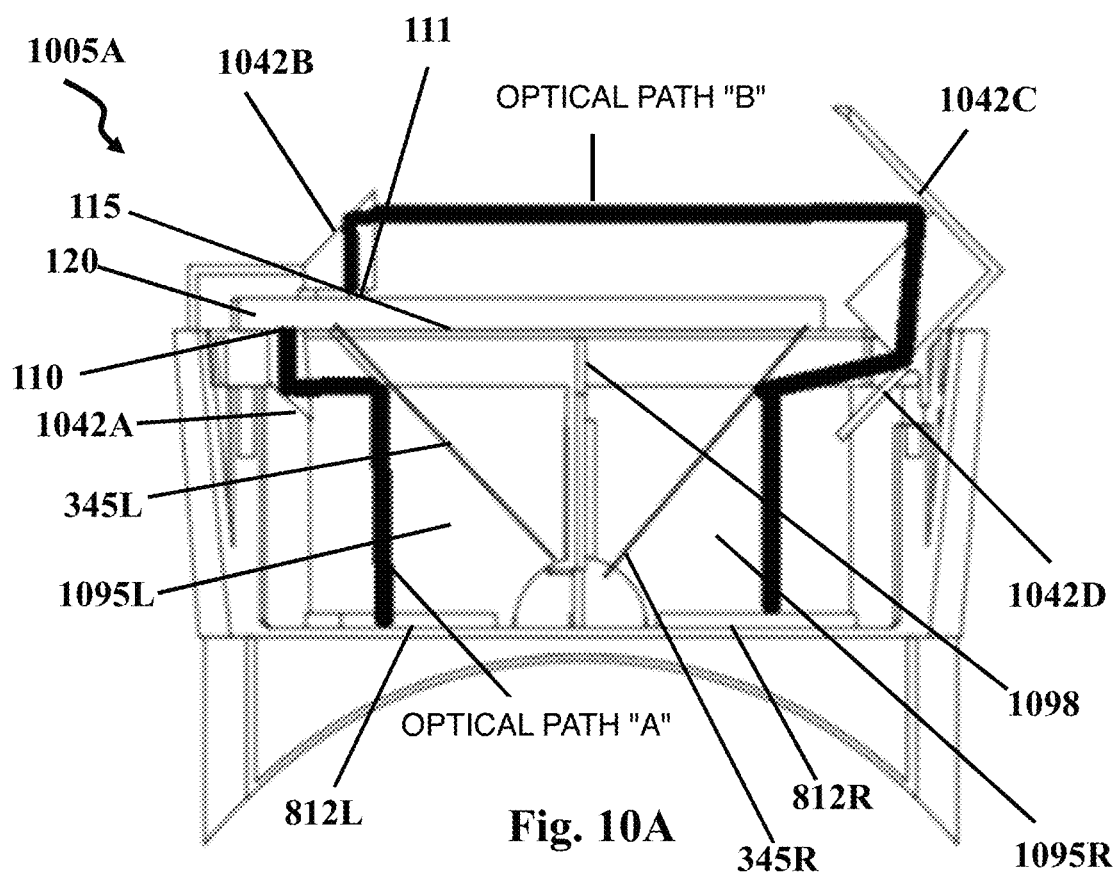
FIGS. 10A and 10B provide perspective views of headset frames in which each viewing lens has its own optical path to the one or more camera lenses of the cellphone, when the cellphone is operatively disposed in the inventive apparatus.
Figure 10B:
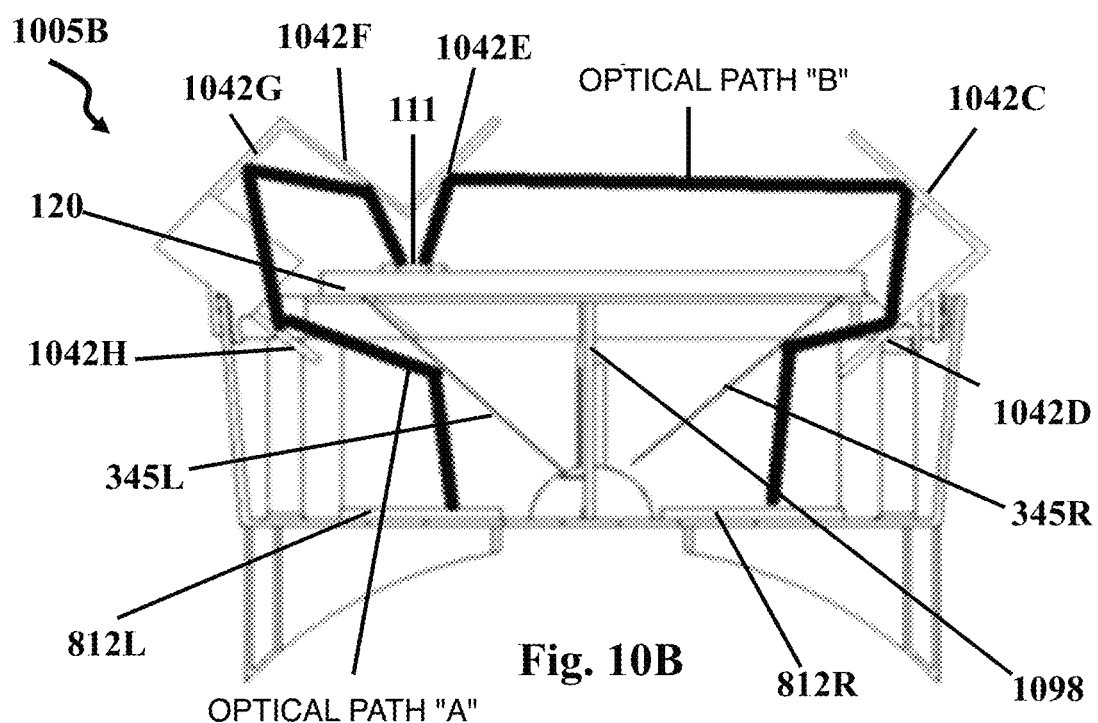

In some embodiments, the beamsplitter may be disposed externally to adaptor arrangement 700, for example, attached or integrally attached to a headset viewing assembly such as headset viewing assembly 305 (shown in FIG. 7A, or as shown in FIGS. 10A-10B, described hereinbelow.

Optical angle modifiers 342A, 342B may be disposed in one or more optical angle modifier housings such as housing 343A and housing 343B. At least one of optical angle modifiers 342A, 342B may be a mirror, and optical angle modifier 342A and housing 343 may form a periscope arrangement.

Adaptor arrangement 700 may further include receiving or affixing means 746 for receiving and securing onboard beamsplitter 345. In the exemplary embodiment provided in FIGS. 7D-7F, receiving or affixing means 746 includes a slot for receiving and securing a first end of onboard beamsplitter 345.

Adaptor arrangement 700 may be secured to a headset viewing assembly or to a main headset body by means of a fastening arrangement. Such a fastening arrangement may include at least one fastener 752. The fastening arrangements may include, but is not limited to, hook and loop arrangements, screw and screwhole, clasp arrangements, pressure fit or snap fit arrangements, etc. Adaptor arrangement 700 may have a perimeter that is substantially in-line with the main headset body (e.g., as shown), or may be dimensioned to fit within the main headset body (as shown in FIG. 7G).

Adaptor arrangement 700 may further include a space (e.g., within slot 772) for receiving a screen filter such as screen filter 517.

FIG. 7G provides a perspective view of a headset frame or headset apparatus frame 705 according to aspects of the present invention. Headset frame 705 may include a rear cover 707 that may optionally be connected to frame 705 by means of a connector 709. In the exemplary embodiment provided in FIG. 7G, connector 709 is a hinge assembly.

Headset frame or headset apparatus frame 705 may include an adaptor arrangement such as adaptor arrangement 700. In the exemplary embodiment provided in FIG. 7G, adaptor arrangement 700A is dimensioned and adapted to fit inside the main housing 790 of headset frame 705.

As shown, screen filter 517 is disposed within headset frame 705, within adaptor arrangement 700A.

The inventors have found that when the user dons the headset, the eye of the user may receive very little light, such that the camera fails to receive a clear image of the eye. The inventors have further found that when a light source is positioned to direct light at the eye of the user, the camera may receive a clear image of the eye, however, this arrangement may cause discomfort and fatigue to the eye, which may also promote non-compliance and errant results.

The inventors have discovered a method and arrangement for enabling the camera of the cellphone to capture a suitable image of the eye. The method includes illuminating the interior of viewing recess 760 in a fairly uniform manner.

With reference now to FIG. 8, FIG. 8 is a schematic drawing of a headset viewing assembly 805 having an illumination arrangement 840, according to aspects of the present invention. Headset viewing assembly 805 includes a viewing recess 760, which is designed and dimensioned to enable a user to juxtapose his face thereto, such that the eyes of the user suitably view a target (e.g., the cellphone screen attached to or disposed within headset viewing assembly 805) via viewing lenses 812.

Viewing recess 760 is enveloped by side walls 861 and 862, by top and bottom walls 863 and 864, and by front wall 865, which houses viewing lenses 812.

Viewing recess 760 may be further designed and dimensioned such that in a viewing mode, with the user juxtaposing his face to walls of viewing recess 760, the face closes off viewing recess 760 so as to form a viewing chamber. This viewing chamber may be substantially sealed, from a lighting standpoint, from the outside environment.

In some embodiments, a lighting arrangement 875 is disposed within viewing recess 760. Lighting arrangement 875 may include at least one light source 840, typically a two-lead semiconductor light source such as a light-emitting diode (LED), as well as a power source such as a battery (not shown). The light source may be from the cellphone itself, as described with respect to FIGS. 9A-9B.

An LED is extremely efficient from an energy standpoint, and emits little heat. However, such an LED emits directional light, which may be disadvantageous, as described above. The LED may be a surface-mount device (SMD) LED module that uses surface-mount technology to mount one or more LED chips on a printed circuit board. The LED may be a self-contained surface-mount LED device. Those of skill in the art will appreciate that other suitable types of LED may be utilized.

Lighting arrangement 875 may further include a light diffuser or light diffuser plate 841 optically disposed between the optical path of light source 840 and the eye of the user, when in viewing mode (with the lighting arrangement in an operative or "on" mode). Light diffuser plate 841, which is typically translucent, may be made of plastic or other materials known to those of skill in the art, and may extend from front wall 865, towards the open face of headset viewing assembly 805. Light source 840 may be held by, or affixed to, light diffuser 841. The inventors have further discovered that by directing light source 840 away from the light diffuser, in the direction of an interior wall of viewing recess 760 (e.g., wall 861), the light may be yet more appreciably diffused, relative to an arrangement in which light source 840 is directed towards light diffuser 841.

FIG. 8A provides a schematic top cross-sectional view of a portion of headset viewing assembly in which the illumination arrangement 875 includes a diffuser plate 841, as described above. In some embodiments, at least part of, or most of, the interior walls (e.g., wall 861) of viewing recess 760 have a diffuse reflective surface (i.e., facing towards viewing recess 760) made of a diffuse reflective material that minimize or appreciably reduce specular reflection, and allow appreciable diffuse reflection. For example, such a diffuse reflective surface may have coated by a white matte paint.

In some embodiments, a material having reflective properties is made with an irregular surface, so as to reflect incident light rays in many directions.

The plastic that is used in the eye area may advantageously be white and highly reflective, for the reasons provided above.

Figure 9A:
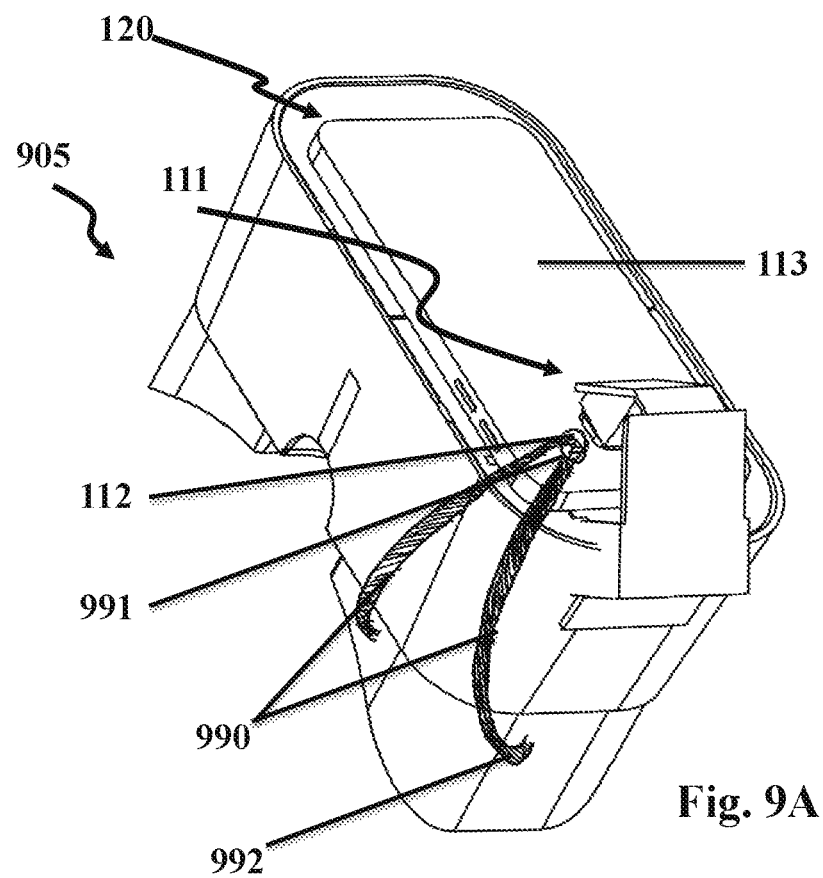
FIGS. 9A and 9B provide perspective views of a headset frame in which the light source includes a flash unit associated with the lens of the cellphone's secondary camera, and in which an optical arrangement may form an optical path from the rear camera lens, towards the viewing lens of the headset frame viewing recess.
Figure 9B:
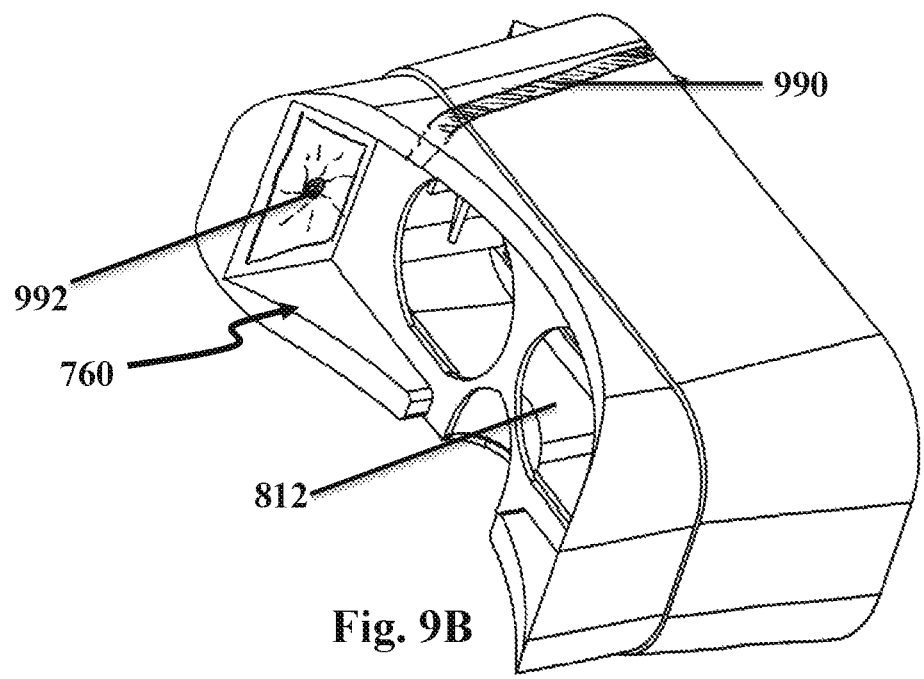

According to aspects of the present invention, FIGS. 9A and 9B provide perspective views of a headset frame 905 in which the light source for the headset frame is, or may optionally include, a flash unit 112 associated with lens 111 of the secondary camera of cellphone 120. The rear cover of headset frame 905 is not shown, in order to reveal cellphone 120 along with the inner workings of headset frame 905 pertaining thereto. Typically, lens 111 of this secondary camera is disposed on a rear side 113 of cellphone 120.

In some embodiments, at least one optical fiber cable 990 is disposed such that a first end 991 receives light (when the flash or flashlight is in operative mode) from flash unit 112. The opposite end 992 of cable 990 is disposed within viewing recess 760 (best seen in FIG. 9B), so as to illuminate the eye, when viewing via viewing recess 760. In some embodiments, a light diffusing material may be placed at end 992 of the optical fiber in cable 990, such that the light within viewing recess 760 is more diffuse.

In some embodiments, the optical arrangement of FIG. 8A may also be implemented with optical fiber cable 990, e.g., with at end 992 of cable 990 being supported by light diffuser 841, and with the light delivered from the optical fiber being directed towards a wall of viewing recess 760. No additional LED is required.

According to aspects of the present invention, FIG. 9A further provides a perspective view of a headset frame 905 in which lens 111 of the secondary camera is disposed on rear side 113 of cellphone 120, and in which an optical arrangement 975 forms an optical path from lens 111, around a side of cellphone 120, and towards a viewing lens 812 (shown in FIG. 9B) of viewing recess 760.

FIGS. 10A and 10B provide perspective views of headset frames 1005A, 1005B, in which each eye or viewing lens has its own optical path to the one or more camera lenses of the cellphone, when suitably disposed in the inventive apparatus.

The apparatus may include an (opaque) internal separator or partition 1098 (typically generally perpendicular to screen 115 of cellphone 120, and/or generally perpendicular to left and right viewing lenses 812L and 812R) adapted to divide the optical chamber (containing the various optical paths) so as to provide each eye with a respective optically isolated optical chamber 1095L, 1095R (such that no or substantially no light passes from chamber to chamber). Such an internal separator and optically isolated optical chambers may be operative for all optical chambers of the present invention. Generally speaking, the internal walls within an optical chamber may preferably be light-absorbing walls that are preferably black and/or preferably non-reflective/matte, and typically, black and matte.

With specific reference now to FIG. 10A, headset frame 1005A is adapted to utilize front and rear camera lenses of cellphone 120, to provide each eye or viewing lens with an individual, optically distinct and isolated optical path to these camera lenses, when the cellphone is disposed in the inventive apparatus.

Optical path "A" is optically disposed between the left viewing lens 812L (and left viewing eye) and camera lens 110 disposed on the front or screen side of cellphone 120, with cellphone 120 disposed in position, such that screen 115 faces the viewing lenses. Optical path "B" is between the right viewing lens 812R (and right viewing eye) and camera lens 111 disposed on the rear side of cellphone 120. It will be appreciated that left and right are arbitrary, and that the apparatus may be constructed such that Optical path "A" is that of the right viewing lens.

Optical path "A" has at least one optical angle modifier 1042A and a beamsplitter 345L, and may be substantially similar to, or identical to, the optical path described with respect to FIG. 5A.

Optical path "B" includes, between camera lens 111 and right viewing lens 812R, at least three optical angle modifiers 1042B, 1042C, and 1042D, as well as a beamsplitter 345R. Beamsplitter 345R is positioned such that from viewing lens 812R, a portion of the light is reflected by (or the optical path is directed by) beamsplitter 345R, towards optical angle modifier 1042D.

Additional optical paths, each passing through a beamsplitter, have been described hereinabove.

From optical angle modifier 1042D, the optical path is directed to optical angle modifier 1042C, which is disposed behind or distal to cellphone 120. The optical path is directed to optical angle modifier 1042C, which is also disposed behind or distal to cellphone 120, and is further disposed and angled such that the optical path is directed into camera lens 111 disposed on the rear side of cellphone 120.

It will be appreciated that while in both FIGS. 10A and 10B, the rear cover of the headset frames is not shown, for the sake of clarity, all optical paths from the viewing lenses to the cellphone camera lenses and screen are isolated from light from the environment.

With specific reference now to FIG. 10B, headset frame 1005B is adapted to utilize rear camera lens 111 to provide each eye or viewing lens with an individual, optically distinct and isolated optical path to these camera lenses, when the cellphone is disposed in the inventive apparatus.

Optical path "B" may be substantially similar to the optical path described with respect to FIG. 10A. Optical angle modifier 1042E, which parallels the function of 1042B of FIG. 10A, may be dimensioned and angled in a somewhat different manner, however, due to the fact that rear camera lens 111 is part of two distinct optical paths, and in view of spatial considerations.

Optical path "A" includes, between camera lens 111 and left viewing lens 812L, at least three optical angle modifiers 1042F, 1042G, and 1042H, as well as a beamsplitter 345L. Beamsplitter 345L is positioned such that from viewing lens 812L, a portion of the light is reflected by (or the optical path is directed by) beamsplitter 345L, towards optical angle modifier 1042H.

From optical angle modifier 1042H, Optical path "A" is directed to optical angle modifier 1042G, which is disposed behind or distal to cellphone 120. The optical path is directed to optical angle modifier 1042F, which is also disposed behind or distal to cellphone 120, and is further disposed and angled such that the optical path is directed into camera lens 111.

According to further aspects of the invention, the apparatus of the present invention may be used for augmented reality (e.g., in addition to virtual reality). For example, one camera of the cellphone may be used to film an eye of the user, while the other camera (typically on the rear side of the cellphone) may be used to (simultaneously) film the environment, and provide the cyc with the image, e.g., via viewing lens 812.

Methods of use of various apparatus (e.g., virtual-reality apparatus, augmented virtual-reality apparatus) disclosed herein may be applied in various medical and medical-vestibular settings, and in addition, to gaming (e.g., gaming of social media).

For example, a player may use the system to play a virtual reality game that requires eye tracking.

In another exemplary application, social media activity where an avatar (e.g., an electronic image that represents and is manipulated by a computer user in a virtual space and that interacts with other objects in that virtual space) has a differential response if the user is looking at it.

According to another aspect of the invention, there is disclosed a method of determining which eye is being tracked. The method may include inserting the phone into the case or into place within the apparatus, identifying the rotation of the mobile phone (computing device) by means of its accelerometers, so as to determine, by means of the mobile phone processor, which eye is being tracked.

EXAMPLES

Reference is now made to the following examples, which together with the above descriptions, illustrate the invention in a non-limiting fashion.

Example 1

A patient who has suffered from a unilateral peripheral vestibular is sent to vestibular rehabilitation and is fitted with a headset adapted to hold a Google Nexus smartphone running an application, wherein the multi-touch screen of the smartphone is adapted to be a few centimeters from the patient's eyes. The headset presents optical elements and lighting conditions that allow one of the phone's cameras to continuously video at least one of patient's eyes. The application presents a set of visual targets via the phone's screen pointing at the patient and also determines eye position for calibration. Afterwards, a physical therapist sets a protocol comprised of a set of exercises that require the patient to perform head and/or eye movements. The application is adapted to present the exercises in the protocol and to record the patient's responses. The patient is instructed to use the system at home 3 times a day (the protocol set by the therapist determines the time which is generally around 15 minutes), The patient fits the Google Nexus into the headset, opens the application and wears the headset with the phone screen facing patient's face. The app detects the eye via a phone camera and any associated optical elements, checks calibration (and updates if necessary) and starts the exercises in the protocol. The application monitors performance and adjusts the complexity of the exercise in case the performance is too poor or too good. All information about usage, adjustments, responses and technical information (low battery, unexpected closing of the app, etc.) is recorded by the app and uploaded to a central server. As the patient performs the sessions, the relevant performance information is compared to a cohort database to analyze the evolution of the performance in his/her rehabilitation.

Example 2

A nursing home ward has 3 patients. Patient A, age 78, is prone to falling: patient B, age 82, has age-related macular degeneration; and Patient C, age 68, is a woman having multiple sclerosis (MS). Each patient at his/her appointed time fits the same phone into a provided headset, the appropriate app is turned on, and the headset is fit to be worn by the patient, so that the eyes of the patient are opposite to, and in close proximity with the phone screen. The app is adapted to direct the camera at the eye to identify the user (e.g., pattern recognition of the retina) and will load the protocol set for that specific patient. Recorded information and analysis are stored and uploaded initially on the phone and can be automatically added to an electronic health record.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification, including US Patent Publication Nos. 2006/0206175, 2007/0200927, and 2009/0240172, are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A viewing apparatus comprising:
a headset including at least one viewing lens for at least one of the eyes of the user, so as to view a display screen of a mobile computing device,
a holding case adapted to fixedly hold the mobile computing device and to reversibly attach and detach to the headset;
an optical arrangement associated with the holding case and with the headset, and including at least one optical angle modifier and at least one optical splitter;
the headset, the holding case, and the optical arrangement adapted such that, in a viewing mode, in which the mobile computing device is inserted in the holding case, a display screen of the mobile computing device faces the at least one viewing lens of the headset;
wherein the optical arrangement is further adapted to simultaneously establish, in the viewing mode, a first optical path between the at least one viewing lens of the headset and the camera lens of the mobile computing device; and a second optical path between the display screen of the mobile computing device and the at least one viewing lens of the headset;
wherein the at least one optical splitter is optically disposed on the first optical path, between the viewing lens and the at least one optical angle modifier,
wherein the at least one optical splitter is further optically disposed on the second optical path, between the viewing lens and the the display screen of the mobile computing device;
wherein the at least one optical angle modifier is optically disposed on the first optical path, between the at least one optical splitter and the camera lens;
wherein the at least one optical angle modifier is adapted to modify an angle of incident light received via the at least one optical splitter, and to direct the light towards the camera lens;
wherein the at least one optical splitter that is optically disposed on the first optical path includes an intensity beamsplitter;
the viewing apparatus further comprising a cellphone screen filter optically disposed between the cellphone screen and the optical splitter, and adapted and oriented to filter at least a portion of low-angle light emanating from the screen in the direction of the optical angle modifier closest to the camera lens, the low-angle light being at most 50°;
wherein said cellphone screen filter is a cellphone privacy screen filter;
and wherein, at least in the viewing mode, the optical arrangement is disposed in an optical chamber.

2. The apparatus of claim 1, further comprising the mobile computing device, the mobile computing device further including a computer processor adapted, during a viewing event in the viewing mode, to record eye movement information of at least one of the eyes, using the camera lens of the mobile computing device.

3. The apparatus of claim 1, wherein said intensity beamsplitter is regular glass.

4. The apparatus of claim 1, wherein the at least one optical angle modifier includes at least one mirror.

5. The apparatus of claim 1, wherein the headset includes a viewing recess, designed and dimensioned to enable the user to juxtapose his face thereto, said viewing recess adapted such that, with a face of the user juxtaposed thereto in the viewing mode, said viewing recess forms a viewing chamber surrounding the outer surface of said at least one viewing lens.

6. The apparatus of claim 5, further comprising a light source arrangement including a light source disposed within the viewing recess, and adapted, in the viewing mode, to provide light within the viewing recess.

7. The apparatus of claim 6, wherein the light source is directed towards an inner wall of the viewing recess.

8. The apparatus of claim 7, wherein the light source arrangement includes a light diffuser, optically disposed between the light source and at least one of the viewing lens and a position of the eye of the user, when viewing through the viewing lens, in the viewing mode.

9. The apparatus of claim 8, wherein the light source includes a light-emitting diode (LED).

10. The apparatus of claim 6, wherein the light source includes a flash from the cellphone, and the light source arrangement includes an optical conduit for delivering light from the flash to the viewing recess.

11. The apparatus of claim 1, wherein at least one internal wall of the optical chamber is a light-absorbing wall that is black and/or matte.

12. The apparatus of claim 1, wherein said intensity beamsplitter is an element having partial reflectivity within a range of 2-60%.

13. The apparatus of claim 1, wherein said intensity beamsplitter is an element having partial reflectivity within a range of 6-40%.

14. The apparatus of claim 1, wherein the first optical path passes from the viewing lens to said beamsplitter, from said beamsplitter directly to the at least one optical angle modifier, and from the at least one optical angle modifier to the first camera lens of said cellphone.

15. A viewing apparatus comprising:
(a) a headset having at least one viewing lens and adapted to be juxtaposed, in a viewing mode, to a face of a user, such that an eye of the user is aligned with the viewing lens;
(b) an adaptor arrangement adapted to fixedly hold a cellphone equipped with at least one camera lens, and to reversibly attach and detach to the headset, the adaptor arrangement including:
(i) a cellphone receiving arrangement for fixedly receiving the cellphone in a viewing position; and
(ii) an on-board optical arrangement including at least one optical angle modifier; and
(c) an optical splitter, disposed within the viewing apparatus;
the headset, the cellphone receiving arrangement, and the optical arrangement adapted such that, in a viewing mode, in which the adaptor arrangement is reversibly attached to the headset, and in which the cellphone is fixed in the viewing position, a display screen of the cellphone faces the at least one viewing lens of the headset;
wherein the optical splitter and the on-board optical arrangement are adapted to simultaneously establish, in the viewing mode, a first optical path between a first viewing lens of the at least one viewing lens of the headset and at least first camera lens of the at least one camera lens; and a second optical path between the display screen of the cellphone and the first viewing lens;
wherein the optical splitter is optically disposed on the first optical path, between the viewing lens and the at least one optical angle modifier;
wherein the at least one optical angle modifier is optically disposed on the first optical path, between the at least one optical splitter and the first camera lens;
wherein the at least one optical splitter is further optically disposed on the second optical path, between the viewing lens and the the display screen of the mobile computing device;
wherein the at least one optical angle modifier is adapted to modify an angle of incident light received via the at least one optical splitter, and to direct the light towards the first camera lens;
the viewing apparatus further comprising a cellphone screen filter optically disposed between the cellphone screen and the optical splitter, and adapted and oriented to filter at least a portion of low-angle light emanating from the screen in the direction of the optical angle modifier closest to the camera lens, the low-angle light being at most 50°;
and wherein the at least one optical splitter that is optically disposed on the first optical path includes a beamsplitter having partial reflectivity within a range of 2-60%.

16. The apparatus of claim 15, wherein the at least one optical splitter is part of the adaptor arrangement.

17. The apparatus of claim 16, wherein the adaptor arrangement includes at least one fastening element adapted to secure the adaptor arrangement to a complementary fastener element disposed on the headset.

18. The apparatus of claim 16, wherein the adaptor arrangement is adapted to fix a particular cellphone in a single or pre-determined position;
and wherein the camera lens of a particular cellphone is disposed in a particular position, and wherein the adaptor arrangement, including the onboard optical arrangement, is adapted for the particular cellphone and the particular position of the camera lens, such that, with the particular cellphone fixed in the viewing position, the optical angle modifier nearest the camera lens is optically aligned with the camera lens, both being disposed on the first optical path.

19. The apparatus of claim 15, wherein said beamsplitter is a regular glass pane having partial reflectivity.

20. The apparatus of claim 15, wherein the first optical path passes from the viewing lens to said beamsplitter, from said beamsplitter directly to the at least one optical angle modifier, and from the at least one optical angle modifier to the first camera lens of said cellphone.

* * * * *